United States Patent
de la Rama et al.

(10) Patent No.: US 10,857,349 B2
(45) Date of Patent: *Dec. 8, 2020

(54) FLEXIBLE HIGH-DENSITY MAPPING CATHETER TIPS AND FLEXIBLE ABLATION CATHETER TIPS WITH ONBOARD HIGH-DENSITY MAPPING ELECTRODES

(71) Applicant: St. Jude Medical, Cardiology Division, Inc., St. Paul, MN (US)

(72) Inventors: Alan de la Rama, Cerritos, CA (US); Cary K. Hata, Irvine, CA (US); Don Curtis Deno, Andover, MN (US); Carlo Pappone, Cernusco Lombardone (IT)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/898,420

(22) Filed: Jun. 10, 2020

(65) Prior Publication Data

US 2020/0297996 A1   Sep. 24, 2020

Related U.S. Application Data

(63) Continuation of application No. 16/670,678, filed on Oct. 31, 2019, which is a continuation of application
(Continued)

(51) Int. Cl.
*A61B 5/042* (2006.01)
*A61N 1/05* (2006.01)
(Continued)

(52) U.S. Cl.
CPC .......... *A61N 1/0553* (2013.01); *A61B 5/0408* (2013.01); *A61B 5/0422* (2013.01);
(Continued)

(58) Field of Classification Search
CPC .. A61N 1/0551; A61N 1/0553; A61N 1/0476; A61N 1/36071; A61B 5/6852;
(Continued)

(56) References Cited

U.S. PATENT DOCUMENTS

| 4,522,212 A | 6/1985 | Gelinas et al. |
| 5,044,368 A | 9/1991 | Putz |

(Continued)

FOREIGN PATENT DOCUMENTS

| AU | 2015202258 B2 | 5/2015 | |
| CA | 2934209 A1 * | 12/2016 | ............. A61B 18/00 |

(Continued)

*Primary Examiner* — Eun Hwa Kim
(74) *Attorney, Agent, or Firm* — Dykema Gossett PLLC

(57) ABSTRACT

Flexible high-density mapping catheter tips and flexible ablation catheter tips with onboard high-density mapping electrodes are disclosed. These tips can be used for diagnosing and treating cardiac arrhythmias. The flexible, distal tips are adapted to conform to tissue and comprise a plurality of microelectrodes mounted to permit relative movement among at least some of the microelectrodes. The flexible tip portions may comprise a flexible framework forming a flexible array of microelectrodes (for example, a planar or cylindrical array) adapted to conform to tissue and constructed at least in part from nonconductive material in some embodiments. The flexible array of microelectrodes may be formed from a plurality of rows of longitudinally-aligned microelectrodes. The flexible array may further comprise, for example, a plurality of electrode-carrying arms or electrode-carrier bands. Multiple flexible frameworks may be present on a single device. A delivery adapter having an internal compression cone is also disclosed.

20 Claims, 30 Drawing Sheets

Related U.S. Application Data

No. 14/760,682, filed as application No. PCT/US2014/011940 on Jan. 16, 2014, now Pat. No. 10,492,729.

(60) Provisional application No. 61/753,429, filed on Jan. 16, 2013.

(51) Int. Cl.

| | |
|---|---|
| *A61B 5/0408* | (2006.01) |
| *A61N 1/04* | (2006.01) |
| *A61N 1/36* | (2006.01) |
| *A61B 5/00* | (2006.01) |
| *A61B 18/14* | (2006.01) |
| *A61B 34/20* | (2016.01) |
| *A61B 90/00* | (2016.01) |
| *A61B 18/00* | (2006.01) |

(52) U.S. Cl.
CPC .......... *A61B 5/6852* (2013.01); *A61B 5/6859* (2013.01); *A61B 5/6869* (2013.01); *A61B 18/1492* (2013.01); *A61N 1/0476* (2013.01); *A61N 1/0551* (2013.01); *A61N 1/36071* (2013.01); *A61B 2018/00351* (2013.01); *A61B 2018/00577* (2013.01); *A61B 2018/00839* (2013.01); *A61B 2034/2051* (2016.02); *A61B 2090/3966* (2016.02); *A61B 2217/007* (2013.01); *A61B 2218/002* (2013.01)

(58) Field of Classification Search
CPC ... A61B 5/0408; A61B 5/0422; A61B 5/6869; A61B 5/6859; A61B 18/1492; A61B 2018/00351; A61B 2018/00839; A61B 2018/00577

See application file for complete search history.

(56) References Cited

U.S. PATENT DOCUMENTS

| | | |
|---|---|---|
| 5,156,151 A | 10/1992 | Imran |
| 5,450,846 A | 9/1995 | Goldreyer |
| 5,702,438 A | 12/1997 | Avitall |
| 5,836,947 A | 11/1998 | Fleischman et al. |
| 5,846,196 A | 12/1998 | Siekmeyer et al. |
| 5,879,295 A | 3/1999 | Li et al. |
| 5,964,757 A | 10/1999 | Ponzi |
| 6,029,091 A | 2/2000 | de la Rama et al. |
| 6,071,282 A | 6/2000 | Fleischman |
| 6,120,476 A | 9/2000 | Fung et al. |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,216,043 B1 | 4/2001 | Swanson et al. |
| 6,267,746 B1 | 7/2001 | Bumbalough |
| 6,415,187 B1 | 7/2002 | Kuzma et al. |
| 6,430,426 B2 * | 8/2002 | Avitall ............... A61B 5/0422 600/374 |
| 6,477,423 B1 | 11/2002 | Jenkins |
| 6,522,932 B1 * | 2/2003 | Kuzma ................. A61N 1/05 607/116 |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,228,164 B2 | 6/2007 | Fuimaono et al. |
| 7,257,435 B2 | 8/2007 | Plaza |
| 7,412,274 B2 | 8/2008 | Mejia |
| 7,429,261 B2 | 9/2008 | Kunis et al. |
| 7,561,907 B2 | 7/2009 | Fuimaono et al. |
| 8,019,442 B1 * | 9/2011 | Swanson ............... A61N 1/0551 607/117 |
| 8,157,848 B2 | 4/2012 | Zhang et al. |
| 8,271,099 B1 | 9/2012 | Swanson |
| 8,391,947 B2 | 3/2013 | Urman et al. |
| 8,486,063 B2 | 7/2013 | Werneth et al. |
| 8,565,894 B2 | 10/2013 | Vetter et al. |
| 8,603,069 B2 | 12/2013 | Selkee |
| 8,744,599 B2 | 6/2014 | Tegg |
| 8,903,508 B2 | 12/2014 | Feler |
| 9,044,245 B2 | 6/2015 | Condie et al. |
| 9,820,664 B2 | 11/2017 | Hotlink et al. |
| 9,833,608 B2 | 12/2017 | Masson |
| 2001/0047129 A1 | 11/2001 | Hall et al. |
| 2003/0120328 A1 | 6/2003 | Jenkins et al. |
| 2004/0186546 A1 | 9/2004 | Mandrusov et al. |
| 2005/0159741 A1 | 7/2005 | Paul et al. |
| 2007/0123852 A1 * | 5/2007 | Deem ................. A61B 18/1492 606/45 |
| 2007/0219546 A1 | 9/2007 | Mody et al. |
| 2008/0243214 A1 | 10/2008 | Koblish |
| 2008/0319418 A1 | 12/2008 | Chong |
| 2009/0198300 A1 | 8/2009 | Zhang et al. |
| 2009/0240248 A1 | 9/2009 | Deford et al. |
| 2010/0016848 A1 | 1/2010 | Desai |
| 2010/0286684 A1 | 11/2010 | Hata et al. |
| 2011/0106074 A1 | 5/2011 | Kunis et al. |
| 2011/0118726 A1 | 5/2011 | de la Rama et al. |
| 2011/0160721 A1 | 6/2011 | Wang et al. |
| 2011/0190732 A1 | 8/2011 | Majercak et al. |
| 2011/0313417 A1 | 12/2011 | de la Rama et al. |
| 2012/0172697 A1 * | 7/2012 | Urman ................. A61B 5/6858 600/374 |
| 2012/0271302 A1 | 10/2012 | Behl et al. |
| 2012/0296232 A1 | 11/2012 | Ng |
| 2013/0012938 A1 | 1/2013 | Asirvatham et al. |
| 2013/0253504 A1 | 9/2013 | Fang |
| 2013/0274582 A1 | 10/2013 | Afonso et al. |
| 2014/0296902 A1 | 10/2014 | Huszar et al. |
| 2014/0316496 A1 | 10/2014 | Masson et al. |
| 2014/0350564 A1 | 11/2014 | Huszar et al. |
| 2015/0159741 A1 | 6/2015 | Versteyhe et al. |
| 2018/0050190 A1 | 2/2018 | Masson |

FOREIGN PATENT DOCUMENTS

| | | |
|---|---|---|
| CN | 101797181 B | 12/2015 |
| EP | 0779059 A1 | 6/1997 |
| EP | 2752153 A1 | 9/2014 |
| EP | 2732843 B1 | 1/2016 |
| EP | 2664295 B1 | 12/2019 |
| JP | 2009500052 A | 1/2009 |
| JP | 2010057943 A | 3/2010 |
| JP | 2012130392 A | 7/2012 |
| WO | 2007001981 A2 | 1/2007 |
| WO | 2011075328 A1 | 6/2011 |
| WO | 2012092016 A1 | 7/2012 |
| WO | 2015/057521 A1 | 4/2015 |

* cited by examiner

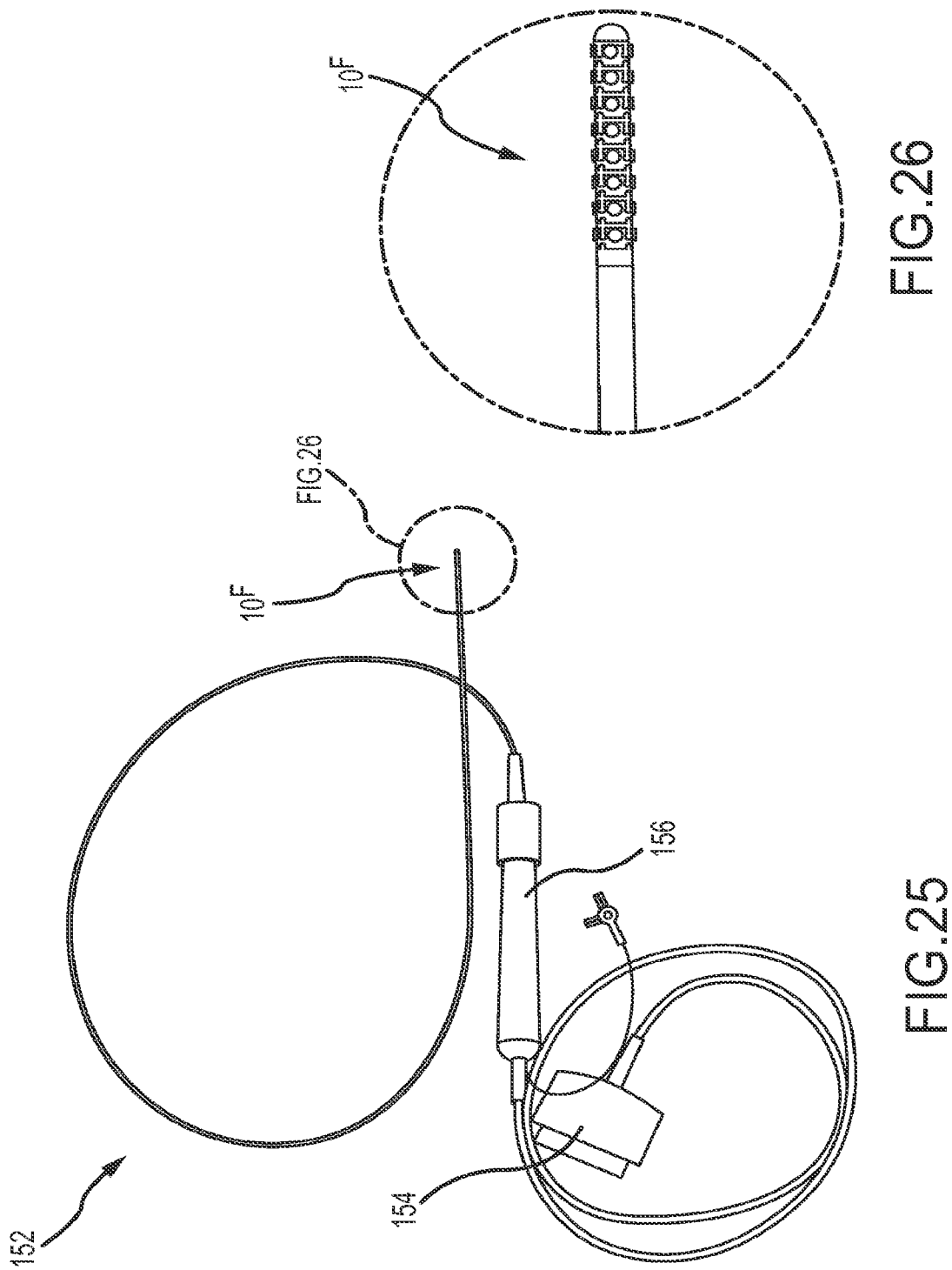

FLEXIBLE HIGH-DENSITY MAPPING CATHETER TIPS AND FLEXIBLE ABLATION CATHETER TIPS WITH ONBOARD HIGH-DENSITY MAPPING ELECTRODES

CROSS-REFERENCE TO RELATED APPLICATIONS

This application is a continuation of U.S. application Ser. No. 16/670,678, filed 31 Oct. 2019, which is a continuation of U.S. application Ser. No. 14/760,682, filed 13 Jul. 2015, now U.S. Pat. No. 10,492,729, issued 3 Dec. 2019, which is a national stage filing based upon international application no. PCT/US2014/011940, filed 16 Jan. 2014 and published in English on 24 Jul. 2014 under international publication no. WO 2014/113612 A1, which claims priority to U.S. provisional application No. 61/753,429, filed 16 Jan. 2013. This application is related to U.S. provisional application No. 60/939,799, filed 23 May 2007; U.S. application Ser. No. 11/853,759, filed 11 Sep. 2007, now U.S. Pat. No. 8,187,267, issued 29 May 2012; U.S. provisional application No. 60/947,791, filed 3 Jul. 2007; U.S. application Ser. No. 12/167,736, filed 3 Jul. 2008, now U.S. Pat. No. 8,206,404, issued 26 Jun. 2012; U.S. application Ser. No. 12/667,338, filed 20 Jan. 2011 (371 date), published as U.S. patent application publication no. US 2011/0118582 A1, now U.S. Pat. No. 8,827,910, issued 9 Sep. 2014; U.S. application Ser. No. 12/651,074, filed 31 Dec. 2009, published as U.S. patent application publication no. US 2010/0152731 A1, now U.S. Pat. No. 8,979,837, issued 17 Mar. 2015; U.S. application Ser. No. 12/436,977, filed 7 May 2009, published as U.S. patent application publication no. US 2010/0286684 A1; U.S. application Ser. No. 12/723,110, filed 12 Mar. 2010, published as U.S. patent application publication no. US 2010/0174177 A1, now U.S. Pat. No. 8,734,440, issued 27 May 2014; U.S. provisional application No. 61/355,242, filed 16 Jun. 2010; U.S. application Ser. No. 12/982,715, filed 30 Dec. 2010, published as U.S. patent application publication no. US 2011/0288392 A1, now U.S. Pat. No. 8,974,454, issued 10 Mar. 2015; U.S. application Ser. No. 13/159,446, filed 14 Jun. 2011, published as U.S. patent application publication no. US 2011/0313417 A1; international application no. PCT/US2011/040629, filed 16 Jun. 2011, published as international publication no. WO 2011/159861 A2; U.S. application Ser. No. 13/162,392, filed 16 Jun. 2011, published as U.S. patent application publication no. US 2012/0010490 A1; and U.S. application Ser. No. 13/704,619, filed 16 Dec. 2012 (371 date), which is a national phase of international patent application no. PCT/US2011/040781, filed 16 Jun. 2011, published as international publication no. WO 2011/159955 A1. Each of these applications is hereby incorporated by reference as though fully set forth herein.

BACKGROUND a. Field

The instant disclosure relates to high-density mapping catheter tips and to map-ablate catheter tips for diagnosing and treating cardiac arrhythmias via, for example, radiofrequency (RF) ablation. In particular, the instant disclosure relates to flexible high-density mapping catheter tips, and to flexible ablation catheter tips that also have onboard high-density mapping electrodes.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

The instant disclosure relates to high-density mapping catheter tips and to map-ablate catheter tips for diagnosing and treating cardiac arrhythmias via, for example, RF ablation. In particular, the instant disclosure relates to flexible high-density mapping catheter tips, and to flexible ablation catheter tips that also have onboard high-density mapping electrodes. Some embodiments include irrigation.

In one embodiment, a high-density mapping catheter comprises an elongated catheter body comprising a proximal end and a distal end, and defining a catheter longitudinal axis extending between the proximal and distal ends; and a flexible, distal tip assembly at the distal end of the catheter body and adapted to conform to tissue, the flexible distal tip assembly comprising a plurality of microelectrodes mounted so that at least some of the microelectrodes are moveable relative to other of the microelectrodes.

In another embodiment, a high-density mapping catheter comprises the following: (i) a catheter shaft comprising a proximal end and a distal end, the catheter shaft defining a catheter shaft longitudinal axis extending between the proximal end and the distal end; (ii) a flexible tip portion located adjacent to the distal end of the catheter shaft, the flexible tip portion comprising a flexible framework comprising nonconductive material; and (iii) a plurality of microelectrodes mounted on the flexible framework and forming a flexible array of microelectrodes adapted to conform to tissue; wherein the flexible framework is configured to facilitate relative movement among at least some of the microelectrodes relative to other of the microelectrodes; and wherein the nonconductive material insulates each microelectrode from other microelectrodes. The flexible array of microelectrodes may be, for example, a planar or cylindrical array of microelectrodes formed from a plurality of rows of longitudinally-aligned microelectrodes. The flexible array may further comprise, for example, a plurality of electrode-carrying arms or electrode-carrier bands.

In yet another embodiment, a flexible, high-density mapping-and-ablation catheter comprising the following: (a) a catheter shaft comprising a proximal end and a distal end, the catheter shaft defining a catheter shaft longitudinal axis; (b) a first plurality of microelectrodes mounted on a first flexible framework of nonconductive material and forming a first flexible array of microelectrodes adapted to conform to tissue; wherein the first flexible framework is configured to facilitate relative movement among at least some of the microelectrodes; and wherein the nonconductive material insulates each microelectrode from other microelectrodes; and (c) a flexible tip portion located adjacent to the distal end of the catheter shaft, the flexible tip portion comprising a second flexible framework constructed from conductive material.

In another embodiment, a flexible, high-density mapping-and-ablation catheter comprising the following: (i) a catheter shaft comprising a proximal end and a distal end, the catheter shaft defining a catheter shaft longitudinal axis; (ii) a first plurality of microelectrodes mounted on a first flexible framework of nonconductive material and forming a first flexible array of microelectrodes adapted to conform to tissue; wherein the first flexible framework is configured to facilitate relative movement among at least some of the microelectrodes in the first plurality of microelectrodes relative to other of the microelectrodes in the first plurality of microelectrodes; and wherein the nonconductive material insulates each microelectrodes in the first plurality of microelectrodes from other microelectrodes in the first plurality of microelectrodes; (iii) a second plurality of microelectrodes mounted on a second flexible framework of nonconductive material and forming a second flexible array of microelectrodes adapted to conform to tissue; wherein the second flexible framework is configured to facilitate relative movement among at least some of the microelectrodes in the second plurality of microelectrodes relative to other of the microelectrodes in the second plurality of microelectrodes; and wherein the nonconductive material insulates each microelectrodes in the second plurality of microelectrodes from other microelectrodes in the second plurality of microelectrodes; and (iv) an ablation region located between the first flexible framework and the second flexible framework.

In still another embodiment, a delivery adapter comprises a body that comprises a dilator support pocket, an internal compression cone, and a guide sheath connector. The delivery adapter body may be separable or splittable into a first portion and a second portion.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 25 depicts an entire high-density mapping catheter according to the sixth embodiment, including an electrical connector and a control handle toward the proximal end of the catheter.

FIG. 26 is similar to FIGS. 23 and 24, and shows an enlarged view of the circled portion of FIG. 25.

DETAILED DESCRIPTION OF EMBODIMENTS

Several embodiments of flexible, high-density mapping catheters and map-ablate catheters are disclosed herein. In general, the tip portions of these various catheters comprise an underlying support framework that is adapted to conform to and remain in contact with tissue (e.g., a beating heart wall). Details of the various embodiments of the present disclosure are described below with specific reference to the figures.

Figure 1:
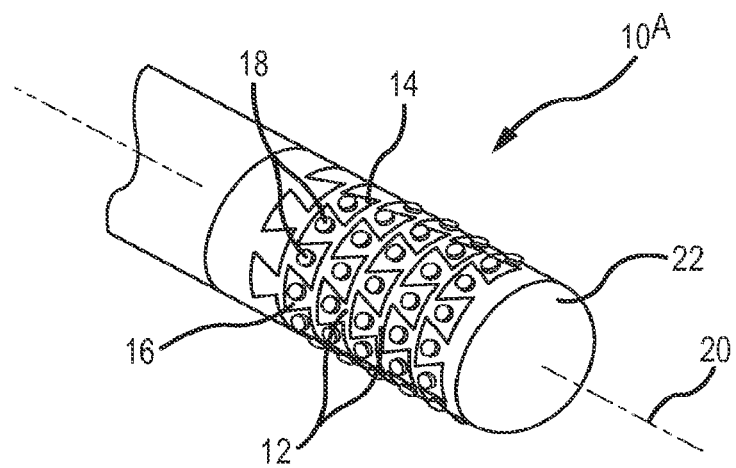
FIG. 1 is a fragmentary, isometric view of a high-density mapping catheter according to a first embodiment.
Figure 2:
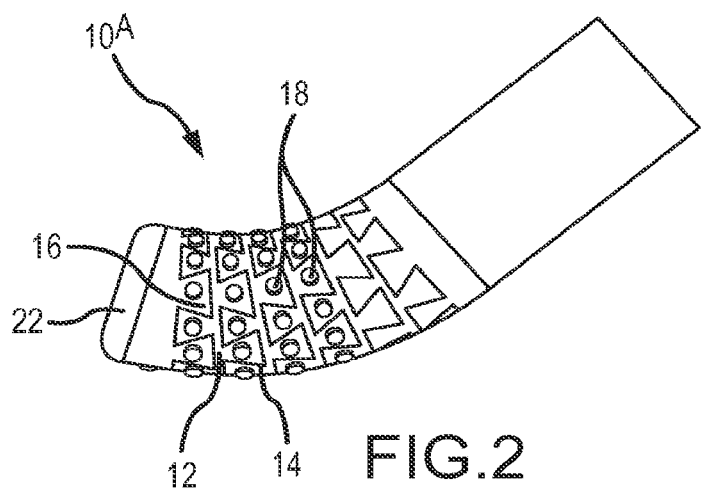
FIG. 2 is an isometric, fragmentary view of the catheter shown in FIG. 1 depicted in a flexed configuration, representing contact between the catheter tip and cardiac tissue.
Figure 3:
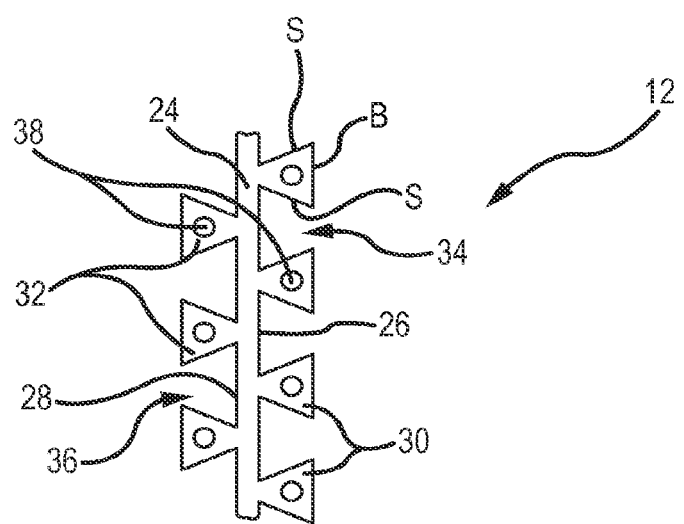
FIG. 3 is a fragmentary view of the flat pattern design of an electrode carrier band (or 'carrier band') according to the first embodiment shown in FIGS. 1 and 2.

FIGS. 1 and 2 depict, and FIG. 3 relates to, a tip portion $10^A$ of a high-density mapping catheter according to a first embodiment. As shown in FIG. 1, the tip portion $10^A$ includes interlocking rings or bands 12 of nonconductive material (e.g., polyether-etherketone or PEEK) forming the underlying support framework for a plurality of microelectrodes. In this embodiment, a circumferential or helical through-cut pattern 14 defines a plurality of dovetail surfaces 16. Each dovetail surface has a microelectrode 18 attached to it, thereby defining a flexible array of microelectrodes that are arranged in circumferential rings or bands. The electrodes 18 are also aligned in longitudinally-extending (e.g., parallel to a catheter longitudinal axis 20) rows of electrodes that are able to flex or move slightly relative to each other during use of the catheter. The nonconductive material individually insulates each microelectrode.

The nonconductive substrate on which the button electrodes 18 are mounted may comprise PEEK. The tip $10^A$ includes a radiopaque tip cap 22 that facilitates fluoroscopy visualization. The tip cap may be domed shaped, hemispherical, flat-topped, tapered, or any other desired general shape.

In this embodiment of the tip portion $10^A$, there are sixty-four discrete microelectrodes 18, and a separate lead (shown in, for example, FIGS. 15 and 16) wire extends to each of these electrodes from the proximal end of the catheter. In a preferred version of this catheter, the catheter is either 7 F or 7.5 F. The flexible tip helps to facilitate and ensure stability during, for example, cardiac motion, which in turn makes it possible to accurately map cardiac electrical activity because of the sustained electrode contact that is possible. The circumferential or helical cuts 14, which may be formed by a laser, create a plurality of serpentine gaps that permit the tip to flex as the cardiac wall moves in a beating heart. When a plurality of circumferential through-cuts are used, this creates a plurality of dovetailed (or 'saw-toothed') bands 12. FIG. 3 depicts the flat-pattern design for one of these bands 12 according to the first embodiment. As clearly shown in FIG. 3, the pattern includes a circumferential waistline or ring 24 defined between a circumferentially-extending proximal edge 26 and a circumferentially-extending distal edge 28. Each of these edges is interrupted by a plurality of proximally-extending pads 30 or distally-extending pads 32. Each pad in this embodiment has the shape of a truncated isosceles triangle with sides S and a base B. Two adjacent proximally-extending pads define a proximally-opening pocket 34 between them. Similarly, on the opposite side of the circumferential waistline 24, two distally-extending pads 32 that are adjacent to each other define a distally-opening pocket 36.

As may be clearly seen in FIGS. 1 and 2, when two of these dovetailed bands are connected, each distally-extending pad 32 flexibly interlocks in a proximally-opening dovetailed pocket 34, and each proximally-extending pad 30 flexibly interlocks in a distally-opening dovetail pocket 36. It is also shown in FIG. 3, each pad 30, 32, in this embodiment, includes an aperture 38 in which a microelectrode will be mounted. Each aperture extends through a pad, from a pad outer surface to a pad inner surface.

Rather than having circumferential through-cuts 14, which define a plurality of individual electrode-carrier bands, the flexible tip depicted in FIGS. 1 and 2 could be formed by a continuous helical cut.

Figure 4:
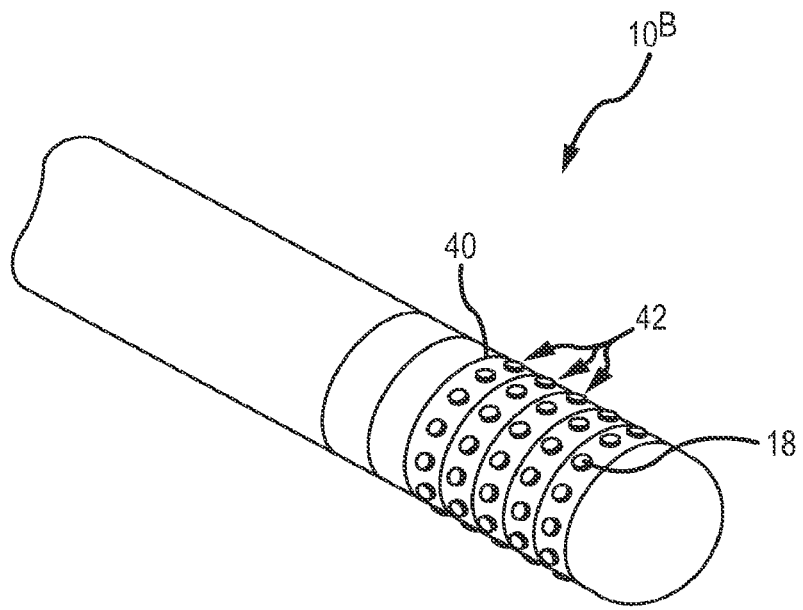
FIG. 4 is a fragmentary, isometric view of a high-density mapping catheter according to a second embodiment.
Figure 5:
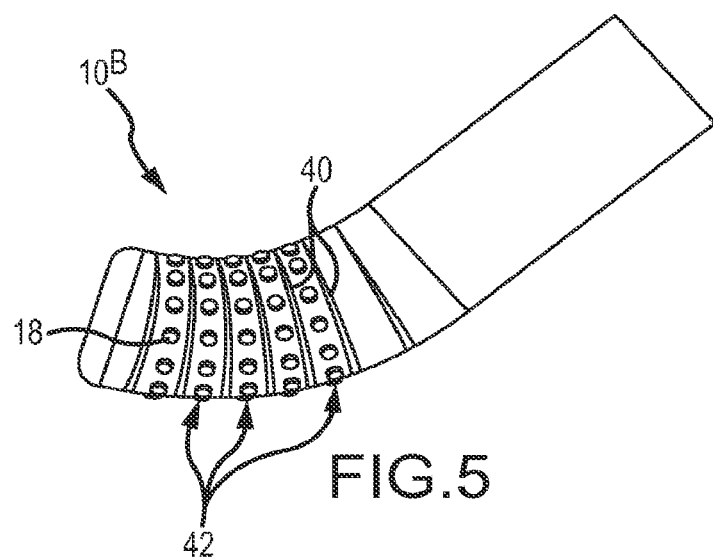
FIG. 5 is a fragmentary, isometric view of the catheter depicted in FIG. 4 shown in a flexed configuration, representing contact between the catheter tip and cardiac tissue.

FIGS. 4 and 5 are similar to FIGS. 1 and 2, respectively, but depict a tip portion $10^B$ of a high-density mapping catheter according to a second embodiment. In this embodiment, circumferential through-cuts 40 define a plurality of discs 42 on which microelectrodes 18 are mounted. Alternatively, a helical cut could be used to form the flexible tip configuration shown in FIGS. 4 and 5. As with the embodiment shown in FIGS. 1 and 2, in the embodiment depicted in FIGS. 4 and 5, the microelectrodes 18 are mounted in a nonconductive material such as PEEK.

Figure 6:
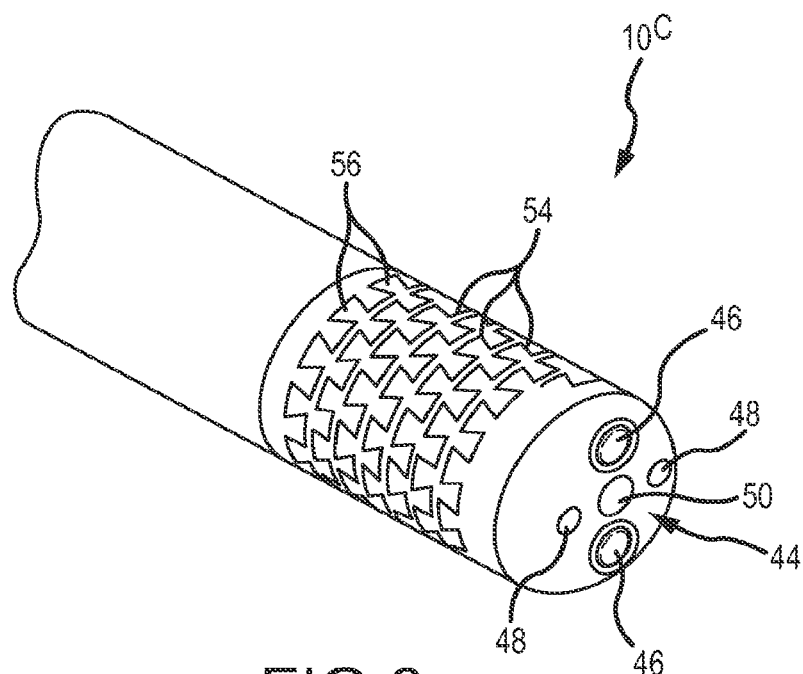
FIG. 6 is a fragmentary, isometric view of a catheter ablation tip having distal high-density mapping electrodes according to a third embodiment.
Figure 7:
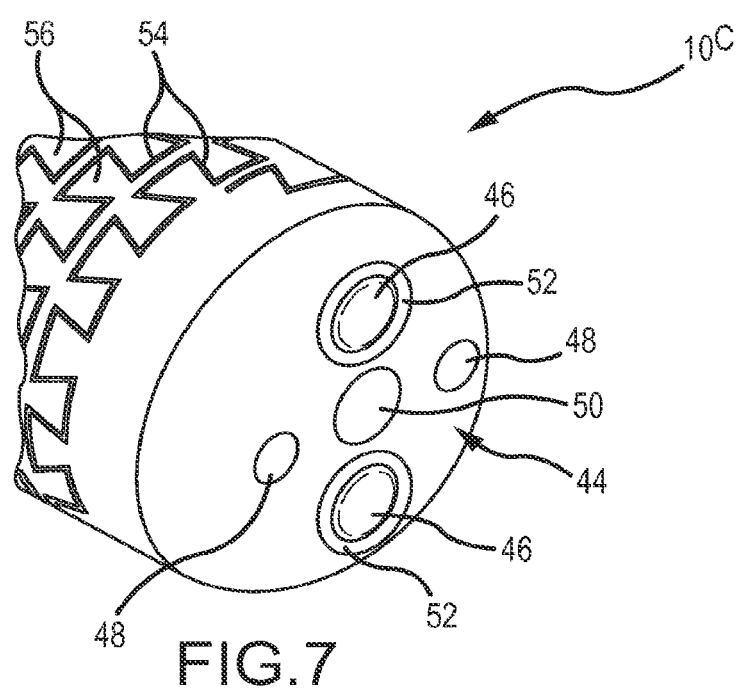
FIG. 7 is an enlarged, fragmentary view of the circled portion of FIG. 6.

A third embodiment of a tip portion $10^C$ is depicted in FIGS. 6 and 7. In this embodiment, however, unlike the embodiment $10^A$ shown in FIGS. 1 and 2, the interlocking, dovetailed pattern is formed from conductive material since this is an ablation tip. As shown to best advantage in FIG. 7, the distal end 44 of this flexible ablation tip includes a pair of symmetrically-placed, high-density microelectrodes 46 for mapping. As also shown to best advantage in FIG. 7, this configuration includes two front-facing irrigation ports 48, and a thermocouple or a temperature sensor 50. The mapping electrodes 46 are mounted in a nonconductive insert 52 to electrically insulate these mapping electrodes from the remainder of the ablation tip. In this particular configuration, the flexible ablation tip is 4 millimeters long. It should also be noted that, in this embodiment, the pads and pockets defined by the serpentine cuts 54 are smaller than the corresponding pads and pockets depicted in, for example, FIGS. 1 and 2. In this ablation tip embodiment $10^C$, the individual pads 56 do not carry microelectrodes and, therefore, the pads can be smaller in this configuration of the ablation tip than they are in the high-density mapping tips.

Figure 8:
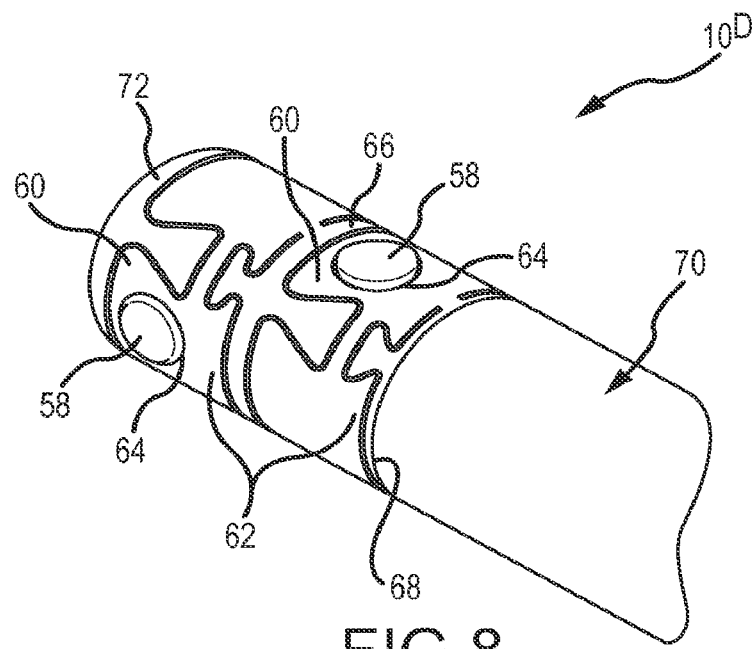
FIG. 8 is a fragmentary, isometric view of an ablation and high-density mapping catheter tip according to a fourth embodiment.
Figure 9:
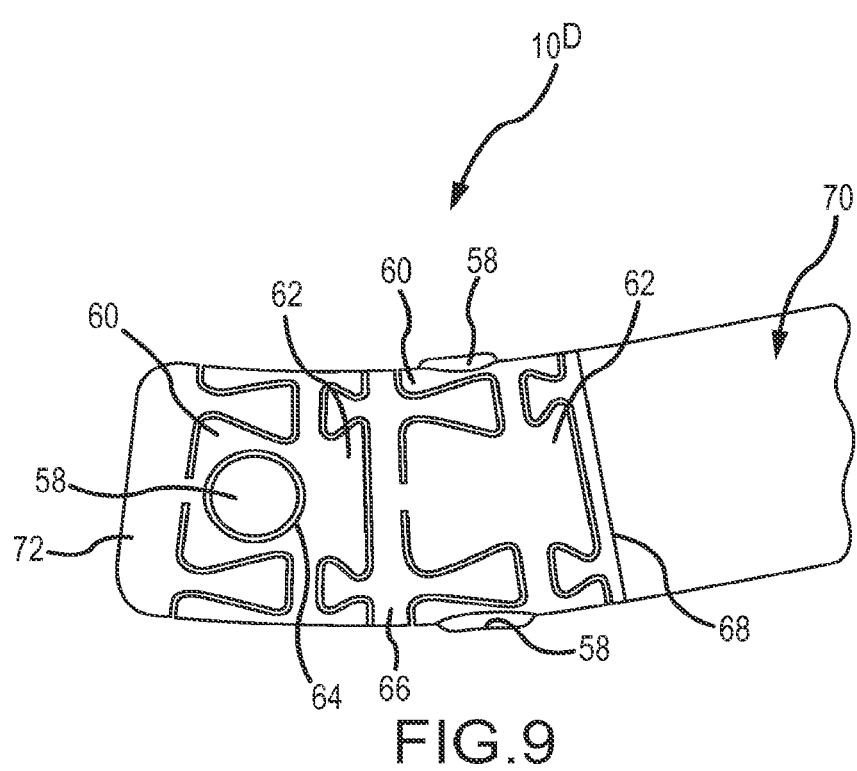
FIG. 9 is a fragmentary, isometric view of the catheter tip depicted in FIG. 8 shown in a partially-flexed or bent configuration, simulating contact between the catheter tip and cardiac tissue.
Figure 10:
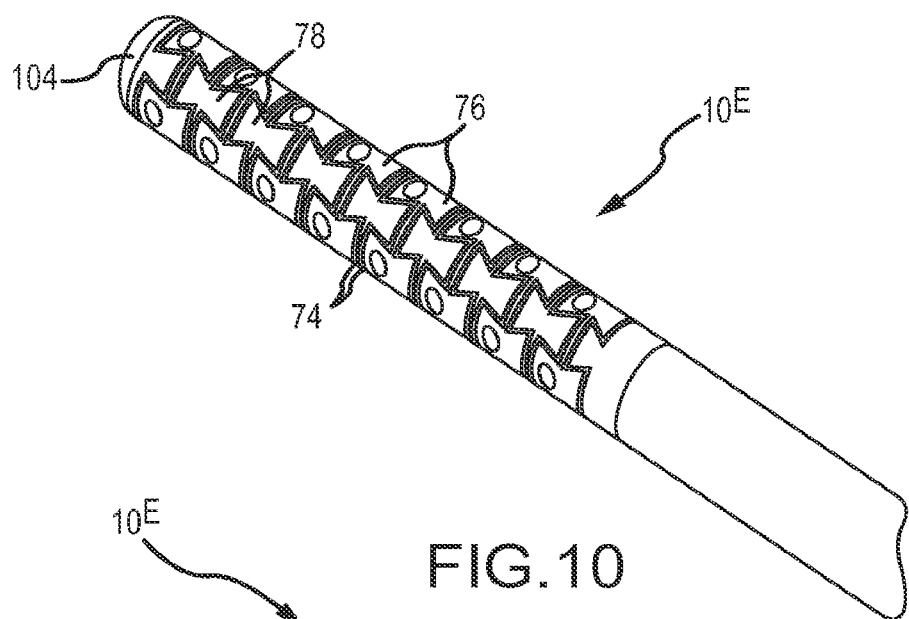
FIG. 10 is a fragmentary, isometric view of a catheter tip of a high-density mapping catheter according to a fifth embodiment.

FIGS. 8 and 9 depict an ablation tip portion $10^D$ and high-density mapping electrode according to a fourth embodiment. This embodiment is a 7.5 Fr catheter having a 4.0 millimeters long, flexible ablation electrode manufactured from, for example, platinum. In this design, four high-density mapping electrodes 58 are mounted through the distal pads 60 of pad structures. Also, each pad structure includes a larger distal pad and a smaller proximal pad 62; and each microelectrode 58 is mounted through an aperture 64 extending through a distal pad 60. In this configuration $10^D$, two carrier bands are interconnected by a linking band 66, a most-proximal carrier band 62 is connected with the distal end 68 of the catheter shaft 70, and a most-distal carrier band is connected to an end cap 72. In this embodiment, each of the four mapping electrodes is individually insulated and has its own lead wire (shown in, for example, FIGS. 5 and 6) extending from the electrode 58 out the proximal end of the catheter. Similar to what occurs in each of the embodiments already discussed, this is an irrigated configuration. Thus, during use of the catheter, irrigant (e.g., cooled saline) is routed from the proximal end of the catheter, through the catheter shaft, and out of the serpentine gaps formed in the tip.

Figure 11:
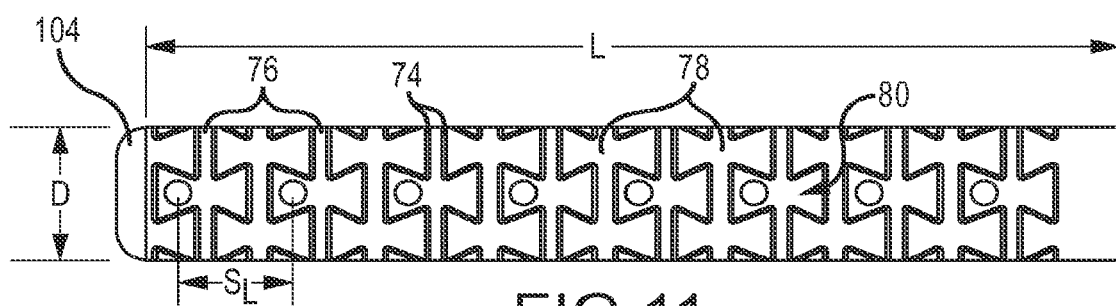
FIG. 11 is a fragmentary, side view of the catheter tip depicted in FIG. 10.

FIGS. 10-16 provide details concerning the tip portion $10^E$ of a high-density mapping catheter according to a fifth embodiment. As shown to good advantage in FIG. 11, this catheter tip $10^E$ gets its flexibility from a plurality of circumferential, dovetail cuts that define a plurality of serpentine gaps 74 between alternating electrode-carrier bands (or carrier bands) 76 and linking bands 78. The working portion of the embodiment $10^E$ depicted in FIG. 11 is approximately 20 millimeters long (see dimension L in FIGS. 11 and 12) and has a diameter of 7 Fr to 7.5 Fr (see dimension D in FIG. 11). In this embodiment, the longitudinal electrode spacing between adjacent microelectrode (see dimension $S_L$ in FIGS. 11 and 12) is approximately 1.8 millimeters, and the circumferential electrode spacing between adjacent microelectrode (see dimension $S_C$ in FIG. 12) is also approximately 1.8 millimeters. An end cap 104 may also be present as shown in, for example, FIGS. 10 and 11.

Figure 12:
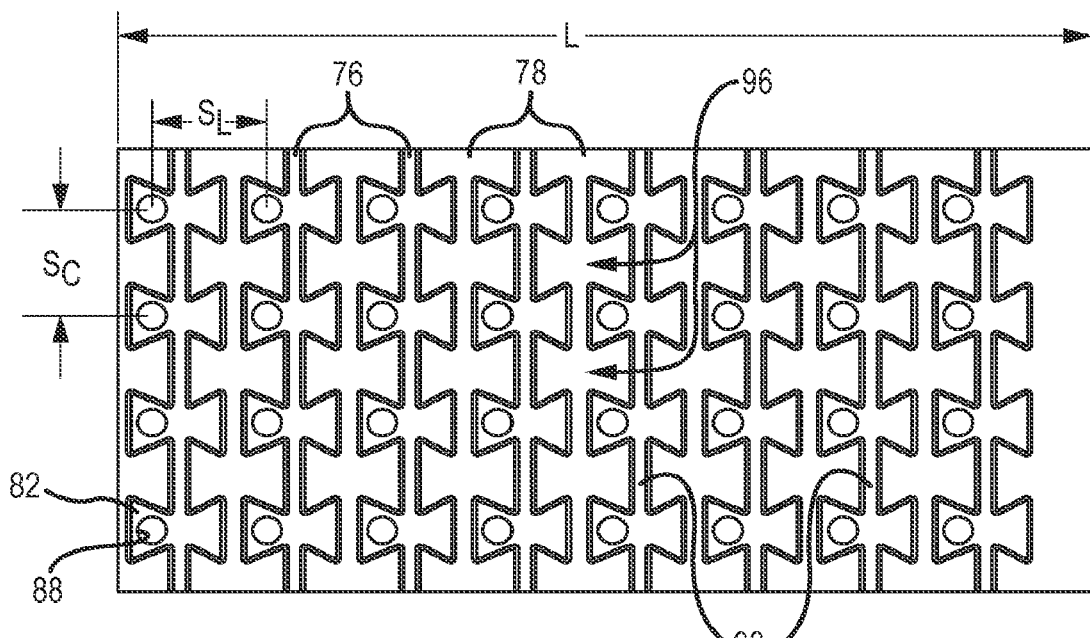
FIG. 12 is a flat pattern design of the materials forming a portion of the catheter tip depicted in FIGS. 10 and 11, clearly showing alternating electrode-carrier bands (or 'carrier bands') separated by a plurality of linking bands.
Figure 13:
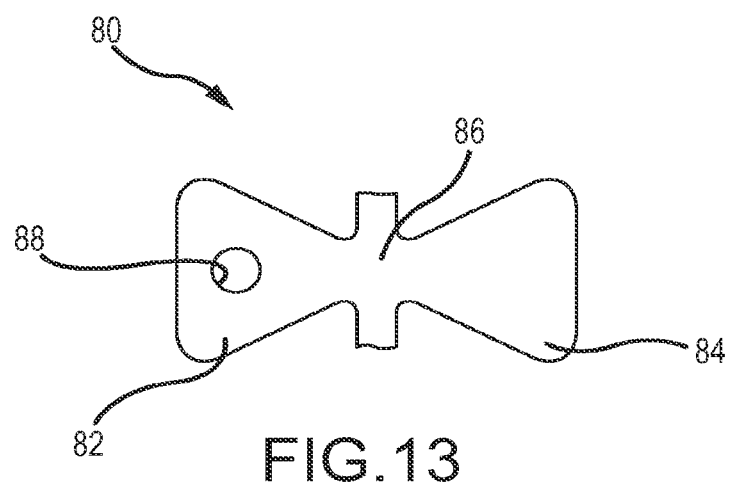
FIG. 13 depicts an isolated pad structure from a carrier band depicted in FIG. 12 and shows the bowtie or hourglass configuration, including a microelectrode mounting aperture.

As shown to good advantage in FIG. 12, the fifth embodiment $10^E$ shows a plurality of electrode-carrier bands 76 separated by a plurality of linking bands 78. Thus, there is one linking band between directly adjacent pairs of carrier bands. In this configuration, each carrier band includes a plurality of bowtie-shaped or hourglass-shaped structures 80 (see for example, FIGS. 13 and 14). Further, in this configuration, each of these bowtie-shaped structures 80 comprises a distal pad 82 and a proximal pad 84, separated by a narrowed region or waist 86. In this configuration, each distal pad 82 of each carrier band 76 has an electrode-mounting aperture 88 (e.g., 0.9 mm diameter) through it.

Figure 14:
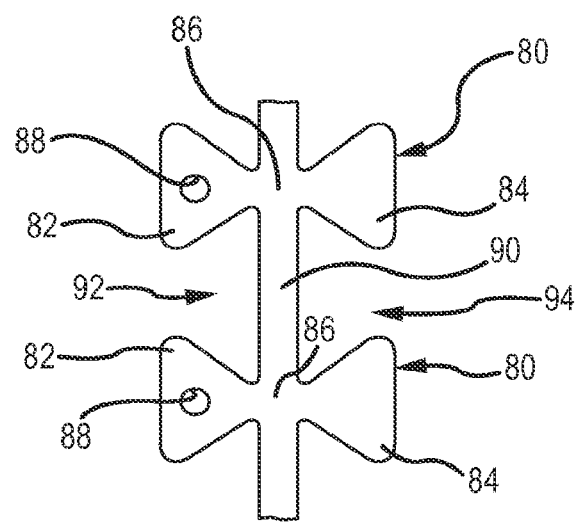
FIG. 14 depicts two pad structures from one of the carrier bands depicted in FIG. 12 including a circumferential connector extending between the pad structures.

Further, as shown to best advantage in FIGS. 12 and 14, there is a circumferential connector 90 between each pair of adjacent pad structures. The circumferential connectors 90, along with the waist 86 of each pad structure 80, together define a circumferential ring. In this embodiment, the bowtie-shaped or hourglass-shaped pad structures 80 are essentially symmetrical about the waist 86 except for the existence of an electrode-mounting aperture 88 in each of the distal pads 82.

As shown in FIG. 14, a distally-opening slot 92 is present between adjacent, distally-extending pads 82. Similarly, a proximally-opening slot 94 is present between adjacent, proximally-extending pads 84. Looking at a single electrode-carrier band, the circumferentially-extending pad connectors 90, together with the waists 86 of each pad structure 80, define a carrier band waistline that extends around the circumference of the tip portion $10^E$ of the catheter.

In this configuration, as shown in FIG. 12, each linking band 78 also comprises a connected series of bowtie-shaped structures 96. In this particular embodiment, the bowtie-shaped pad structures 96 of the linking bands 78 are larger than the bowtie-shaped pad structures 80 of the carrier bands 76.

Figure 15:
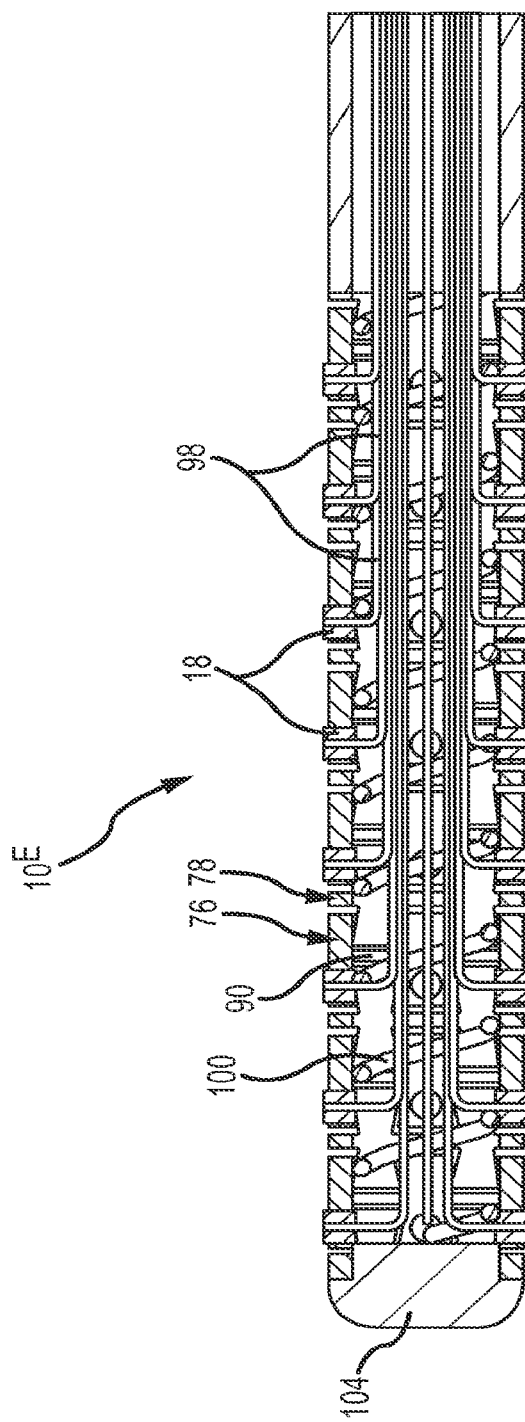
FIG. 15 is a fragmentary view of the distal end of the catheter depicted in, for example, FIGS. 10 and 11, with portions of the catheter removed to reveal internal structures.
Figure 16:
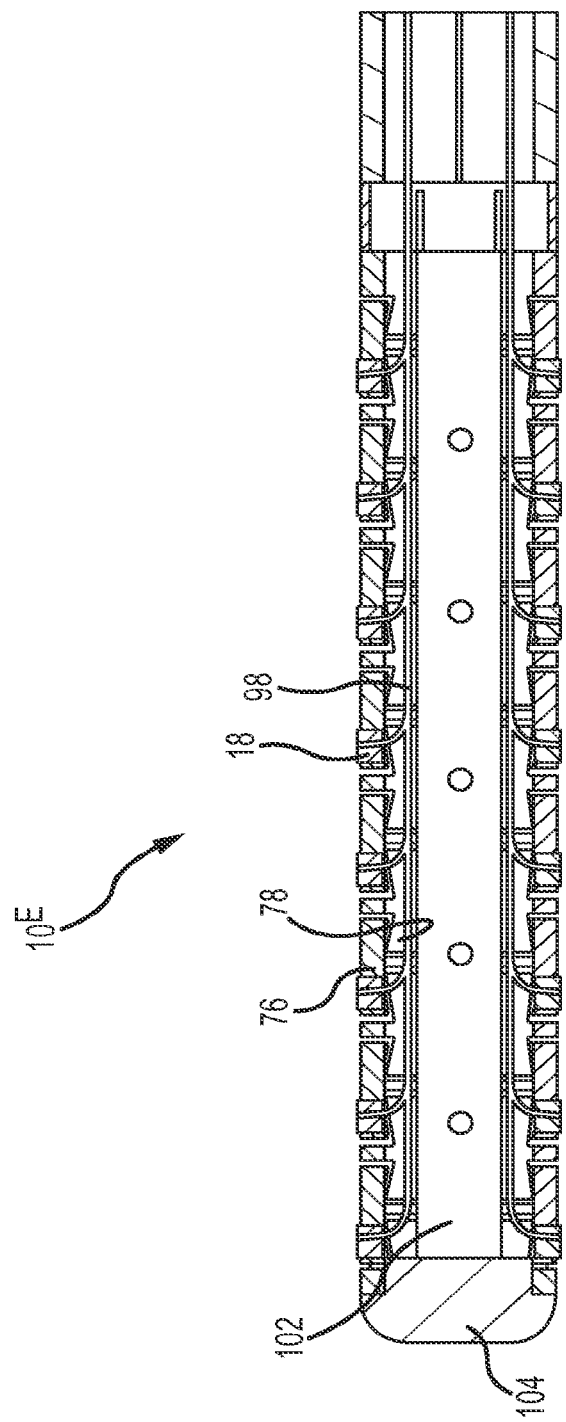
FIG. 16 is similar to FIG. 15, revealing additional internal structures of the catheter tip depicted in, for example, FIGS. 10, 11, and 15.

FIGS. 15 and 16 are views with portions of the catheter removed to show inner details of the catheter tip portion of $10^E$. In FIG. 15, it is possible to see the individual lead wires 98 extending longitudinally through the catheter shaft and connecting with each of the microelectrodes 18. It is also possible to see an internal spring 100 in this figure. This spring helps the tip portion $10^E$ of the catheter maintain its flexibility, and it helps create the gaps between adjacent carrier bands 76 and linking bands 78. FIG. 16 depicts an internal irrigation lumen 102 that acts as an irrigant distribution manifold.

The button electrodes or microelectrodes 18 may have a diameter between 0.7 and 0.9 millimeters. The lead wires extending through the catheter shaft to each of these electrodes may comprise 38 AWG wire. As previously described in connection with other embodiments, an end cap 104 may be metallic, or otherwise radiopaque, to facilitate visualization of the catheter tip during use of a fluoroscope.

Figure 17:
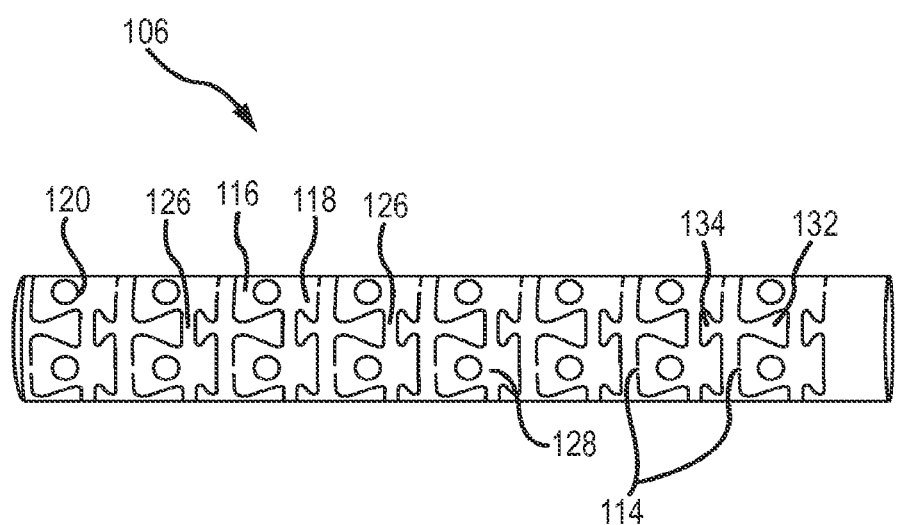
FIG. 17 is a fragmentary view of the tip portion of a high-density mapping catheter according to a sixth embodiment, before the microelectrodes (or 'button electrodes') are mounted.
Figure 18:
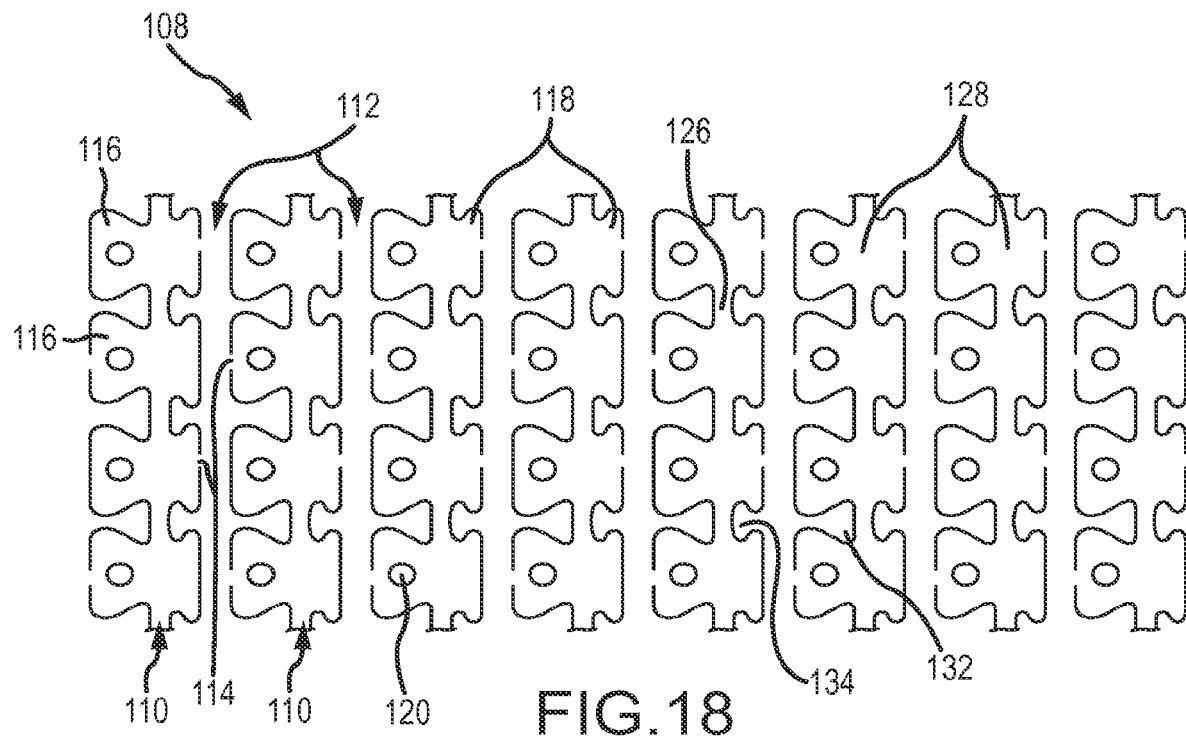
FIG. 18 is similar to FIG. 12, but depicts the flat pattern design used to create the catheter tip depicted in FIG. 17, including electrode-carrier bands (or 'carrier bands'), and linking bands that are slightly different from the corresponding structures depicted in FIG. 12.

FIGS. 17-26 depict aspects of a sixth embodiment of a tip portion $10^F$. FIG. 17 depicts a cylindrical-shaped portion 106 of nonconductive material that has been laser cut to define an interlocking, but flexible pattern 108 (see FIG. 18). FIG. 18 shows what that pattern 108 looks like when it is laid out flat rather than having the cylindrical shape depicted in FIG. 17.

Figure 19:
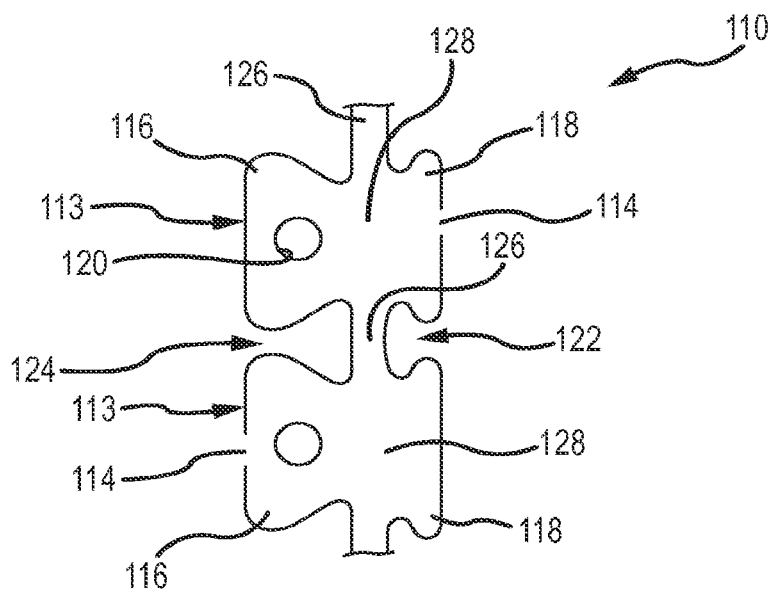
FIG. 19 is similar to FIG. 14, but depicts the pad structures according to the sixth embodiment, including inter-band bridges.

In this embodiment, a plurality of electrode-carrier bands (or carrier bands) 110 and a plurality of linking bands 112 are present. FIG. 19 is similar to FIG. 14, but shows adjacent pad structures 113 according to the sixth embodiment, as also shown in FIGS. 17 and 18. In this configuration, the carrier bands 110 are not completely separate from the adjacent linking bands 112. In particular, as may be clearly seen in FIGS. 17 and 18, this embodiment includes a plurality of inter-band bridges or connectors 114. All of the bands 110, 112 are thereby loosely interconnected, and one band cannot move completely independently of any other band comprising the working portion of the high-density mapping catheter tip $10^F$.

As also clearly shown in FIGS. 17-19, in this embodiment, each pad structure 113 is not the symmetrical bowtie-shaped structure 80 depicted in, for example, FIG. 12. Rather, in the sixth embodiment, the distal tabs 116 of each pad structure 113 are larger than the corresponding proximal pads 118 of the pad structure 113. The electrode apertures 120 extend through this larger distal pad 116.

As shown to good advantage in FIG. 19, slots are formed between adjacent pad structures 113. In particular, a relatively shallow, proximally-opening tab slot 122 is formed between adjacent proximal pads 118. Similarly, a relatively deep, distally-opening tab slot 124 is formed between adjacent pairs of distal pads 116. As described above with reference to FIG. 14, circumferentially-extending connectors 126 are again present between adjacent pad structures 113. All of these connectors on a single carrier band 110, together with the waists 128 of each pad structure comprising part of that same carrier band, form a carrier band waistline.

Figure 20:
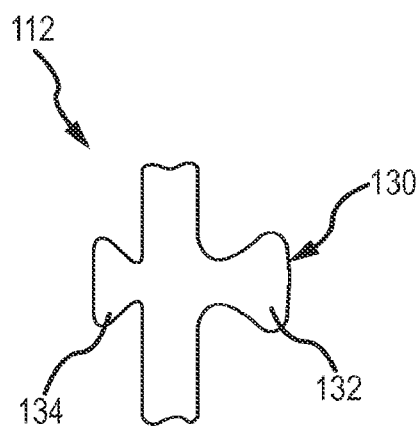
FIG. 20 is a fragmentary view of one tab structure from a linking band depicted in, for example, FIG. 18.
Figure 21:
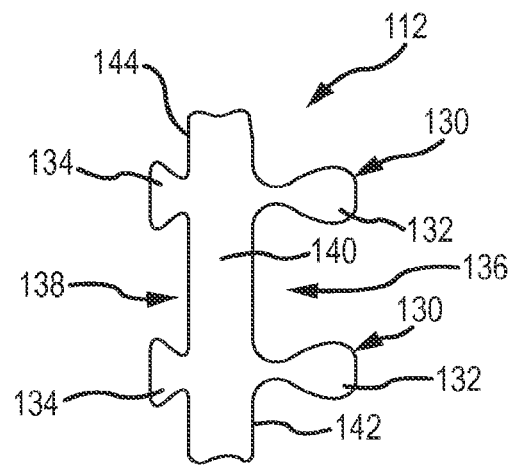
FIG. 21 depicts two tab structures comprising part of a linking band depicted in FIG. 18, including a tab-structure connector extending between the depicted adjacent tab structures.

FIG. 20 depicts a tab structure 130 from a linking band 112. Each linking band comprises a plurality of these tab structures. Each tab structure includes a relatively-longer, proximally-extending tab (or 'proximal tab') 132 in a relatively-shorter, distally-extending tab (or 'distal tab') 134. FIG. 21 depicts two adjacent tab structures 130 of a single linking band 112. A proximally-opening pocket 136 is defined between adjacent proximal tabs 134. Similarly, a distally-opening pocket is defined between adjacent distal tabs. A circumferentially-extending, tab-structure connector 140 connects adjacent tab structures 130 and helps to form the proximally-opening pocket 136 and a distally-opening pocket 138. In other words, each linking band 112 includes a circumferentially-extending proximal edge 142 and a circumferentially-extending distal edge 144. The proximal edge defines a series of proximally-extending tabs 132 and proximally-opening pockets 136, and the distal edge 144 of each linking band 112 forms a plurality of distally-extending tabs and distally-opening pockets 138.

Figure 22:
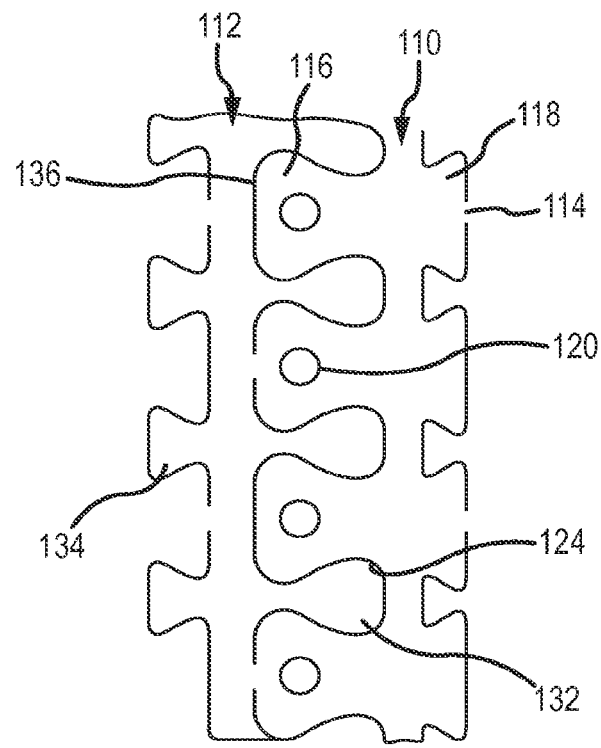
FIG. 22 depicts a single linking band (on the left) interconnected with a single carrier band (on the right) of the design depicted in FIG. 18.

FIG. 22 also relates to the sixth embodiment. In particular, FIG. 22 depicts a single linking band 112 (on the left) flexibly interlocked with a single carrier band 110 (on the right). As shown, each proximally-extending tab 132 is flexibly interlocked in a corresponding distally-opening slot 124 in a carrier band 110. Similarly, each distally-extending pad 116 of the carrier band is flexibly interlocked in a corresponding proximally-opening pocket 136 in the linking band 112.

Each tab structure of the linking band is an asymmetrical bowtie configuration. Similarly, each pad structure 113 of the carrier band 110 is also an asymmetrical bowtie configuration. The serpentine gap extending between the linking band 112 and the carrier band 110 (e.g., a laser cut gap) defines the tabs and the pockets of the linking band, and define the complementary pads and slots, respectively, of the carrier bands.

Figure 23:
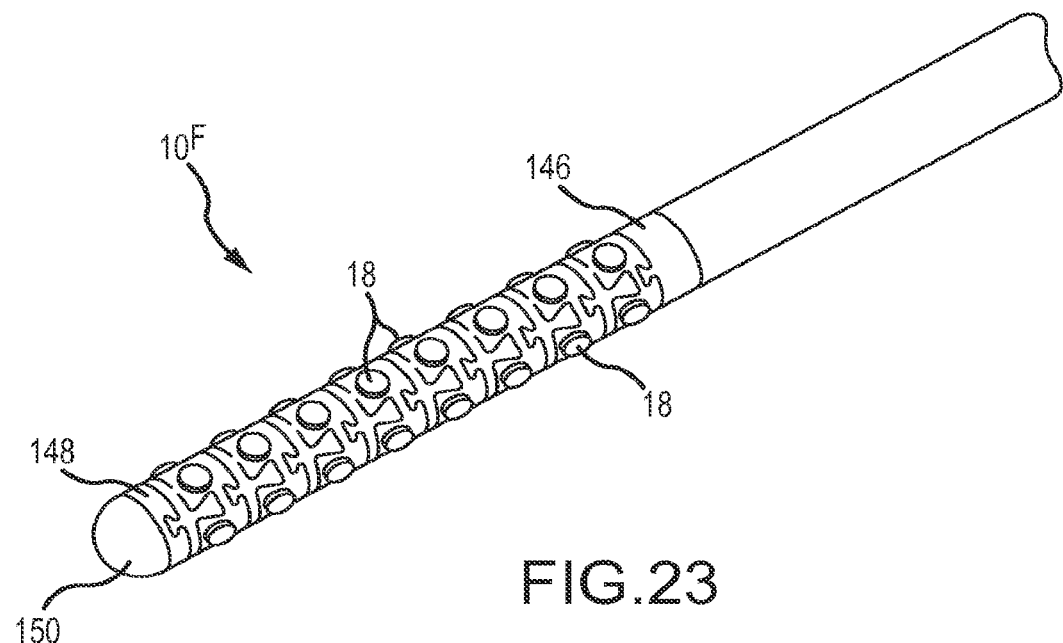
FIG. 23 is a fragmentary, isometric view of the tip of a high-density mapping catheter according to the sixth embodiment, shown with the thirty-two microelectrodes mounted in the electrode apertures depicted in FIG. 17.
Figure 24:
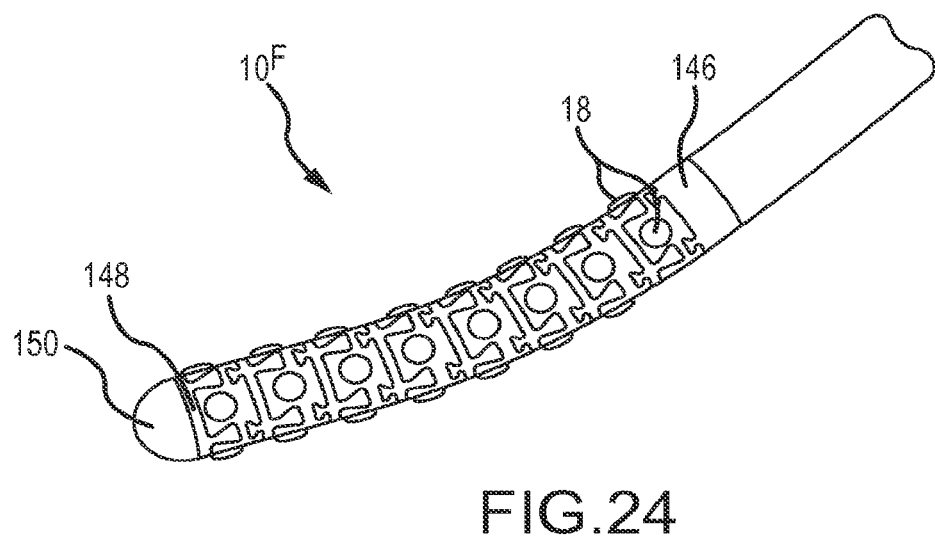
FIG. 24 is an isometric view of the catheter tip depicted in FIG. 23, but shown in a flexed configuration, simulating contact between the catheter tip and a cardiac wall.

FIG. 23 depicts a fully-assembled tip portion $10^F$ of a high-density mapping catheter according to the sixth embodiment. The fully assembled tip includes a most-proximal band (or shaft-transition band) 146, and a most-distal band (or end-cap-transition band) 148. An end cap 150 may be platinum or some other radiopaque material to facilitate visualization on a fluoroscopy screen. As may be seen in FIG. 23, the button electrodes or microelectrodes 18 are slightly raised off the outer surface of the laser cut PEEK material. This is also clearly visible in FIG. 24, which shows the catheter tip in a slightly-flexed configuration. With the electrodes raised slightly as shown, better electrical contact can be maintained between the electrodes and the tissue. In the embodiment depicted in FIGS. 17-26, there are thirty-two mapping electrodes 18 mounted in the laser-cut PEEK material. In this particular design, the catheter shaft is 7 Fr or 7.5 Fr.

FIGS. 25 and 26 also depict the sixth embodiment. In particular, FIG. 25 shows an entire catheter 152, including an electrical connector 154 and a control handle 156 near the proximal portion of the catheter and a flexible high-density mapping tip $10^F$ at the distal end of the catheter 152. FIG. 26 is an enlarged view of the circled portion of FIG. 25.

Figure 27:
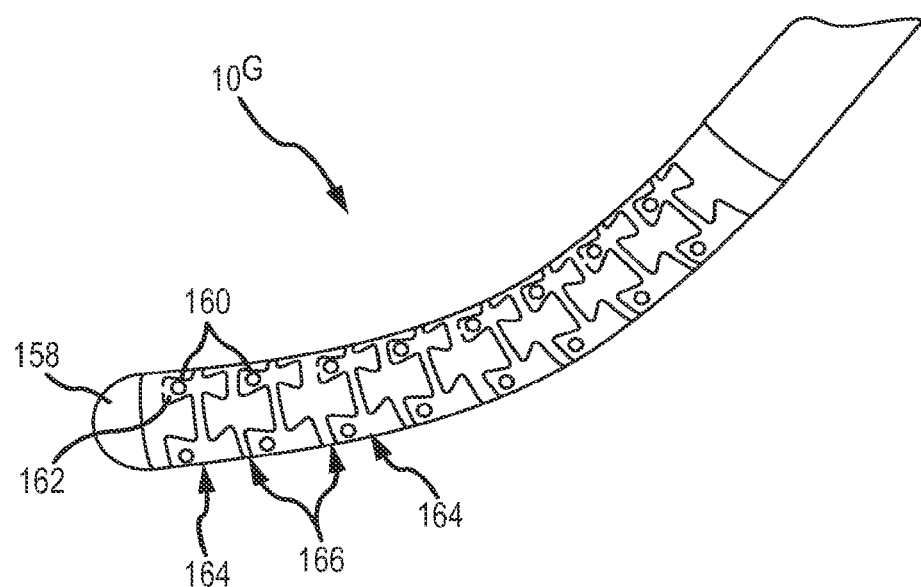
FIG. 27 is a fragmentary, isometric view of the tip portion of a high-density mapping catheter according to a seventh embodiment.

FIG. 27 depicts the distal tip portion $10^G$ of a high-density mapping catheter according to a seventh embodiment. Similar to some of the configurations discussed above, this tip portion includes a metallic cap (e.g., a platinum cap) 158 or otherwise radiopaque cap to facilitate visualization on fluoroscopy. This specific embodiment $10^G$ is different from the embodiment $10^F$ depicted, for example, in FIG. 23, since the electrode apertures 160 in this embodiment are located through the distal pads 162 of pad structures of electrode carrier bands 164 that are relatively smaller than the tab structures of the linking bands 166. In this seventh embodiment, each electrode-carrier band 164 includes a plurality of bowtie-shaped pad structures that are circumferentially arranged around the longitudinal axis of the catheter. Similarly, each linking band 166 comprises a plurality of bowtie-shaped tab structures also arranged circumferentially around the catheter longitudinal axis. In this particular configuration of the tip portion $10^G$, however, the bowtie-shaped tab structures are relatively larger than the bowtie-shaped pad structures of the electrode-carrier bands 164. By changing the relative size of the distal and proximal tabs, and the relative size of the corresponding or related distal and proximal pads, the performance characteristics of the tip portion of the high-density mapping catheter can be adjusted.

Figure 28:
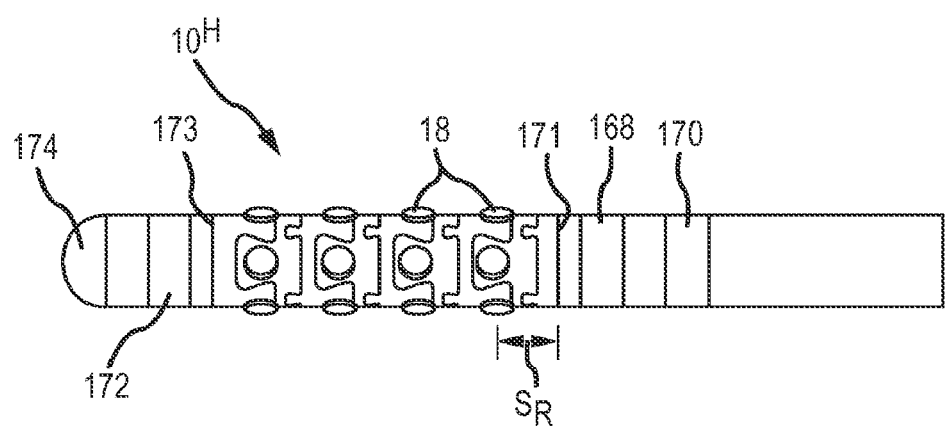
FIG. 28 depicts the distal tip of a high-density mapping catheter according to an eighth embodiment, and includes multiple ring electrodes adjacent to a flexible array of microelectrodes.

FIG. 28 depicts an eighth embodiment of a high-density mapping tip portion $10^H$. In this embodiment, a 7 Fr catheter includes a flexible array of microelectrodes 18 that is similar to, but shorter than, the flexible array of microelectrodes depicted in, for example, FIGS. 23-26. In this particular design, however, 1.0 mm ring electrodes 168, 170, 172 are located at each longitudinal end of the flexible array of 0.9 mm diameter microelectrodes 18. In the depicted embodiment, the most-proximal circumferential ring of microelectrodes 18 is located approximately 1.2 mm (see dimension $S_R$ in FIG. 28) from the most-proximal circumferential edge 171 of array. As shown, there are sixteen microelectrodes arranged in four longitudinally-extending rows of four electrodes, each row radially offset from the next row by 90°. The longitudinal spacing between adjacent microelectrodes may be, for example, 1.8 mm. There are two ring electrodes 168, 170 spaced 1.0 mm from each other and located proximal to the most-proximal circumferential edge 171 of the flexible array of microelectrodes. There is a third 1.0 mm ring electrode 172 located distal of the most-distal edge 173 of the flexible array of microelectrodes. In this particular configuration, there is also a 1.0 mm long metal tip 174 that could be used as an additional electrode.

Figure 29:
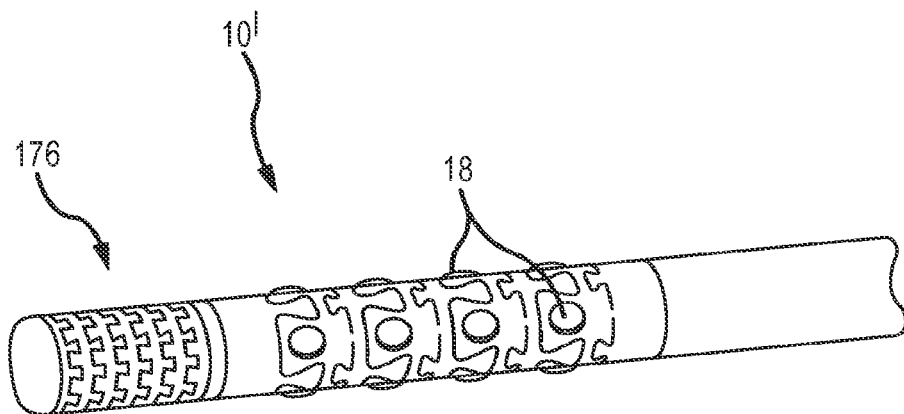
FIG. 29 is a fragmentary, isometric view of the tip portion of a map-and-ablate catheter according to a ninth embodiment, including a flexible array of microelectrodes for mapping and a flexible ablation tip located distal of the flexible array of microelectrodes.
Figure 30:
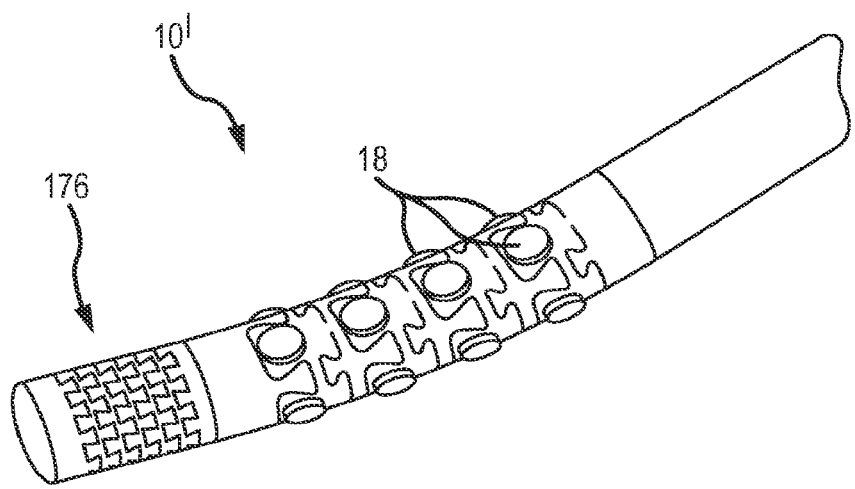
FIG. 30 depicts the catheter tip of FIG. 29 in a partially-flexed configuration, simulating contact between the ablation tip and cardiac tissue.

FIGS. 29 and 30 depict the distal portion $10^I$ of a map-and-ablate catheter according to a ninth embodiment. Similar to what is shown in FIG. 28, the ninth embodiment shown in FIGS. 29 and 30 includes a flexible array of microelectrodes 18 comprising sixteen microelectrodes arranged in four longitudinally extending rows of four where each of these rows is radially offset by 90° from the next adjacent row of electrodes. In this embodiment, however, the most-distal end of the catheter comprises a flexible ablation tip 176. This ablation tip may be, for example, a Cool Flex™ ablation tip sold by St. Jude Medical, Inc. of St. Paul, Minn. During use, irrigant would flow down the catheter shaft and exit through the serpentine gaps in the flexible array of microelectrodes and through the openings in the flexible ablation tip. This tip would advantageously conform to the cardiac tissue during both mapping and ablation procedures.

Figure 31:
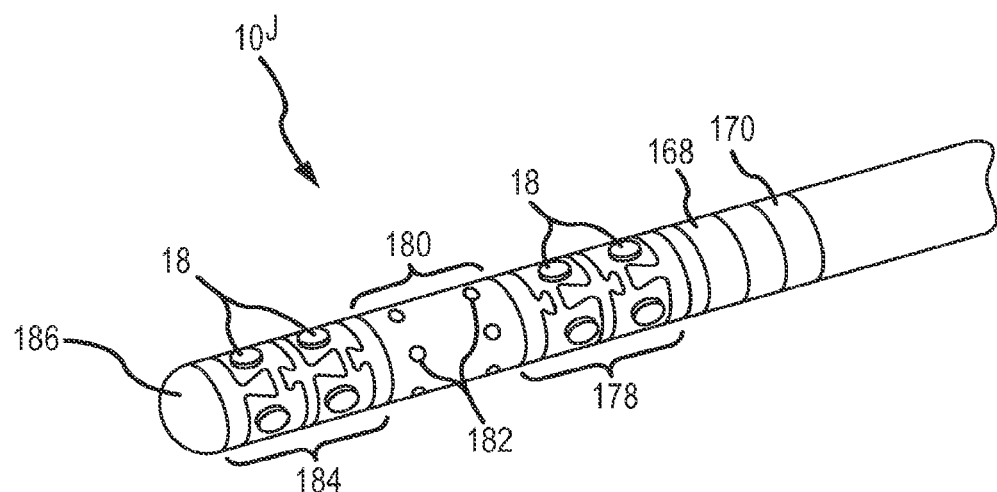
FIG. 31 depicts the tip portion of a map-and-ablate catheter according to a tenth embodiment, including an ablation section straddled by flexible arrays of microelectrodes, and further including two ring electrodes.
Figure 32:
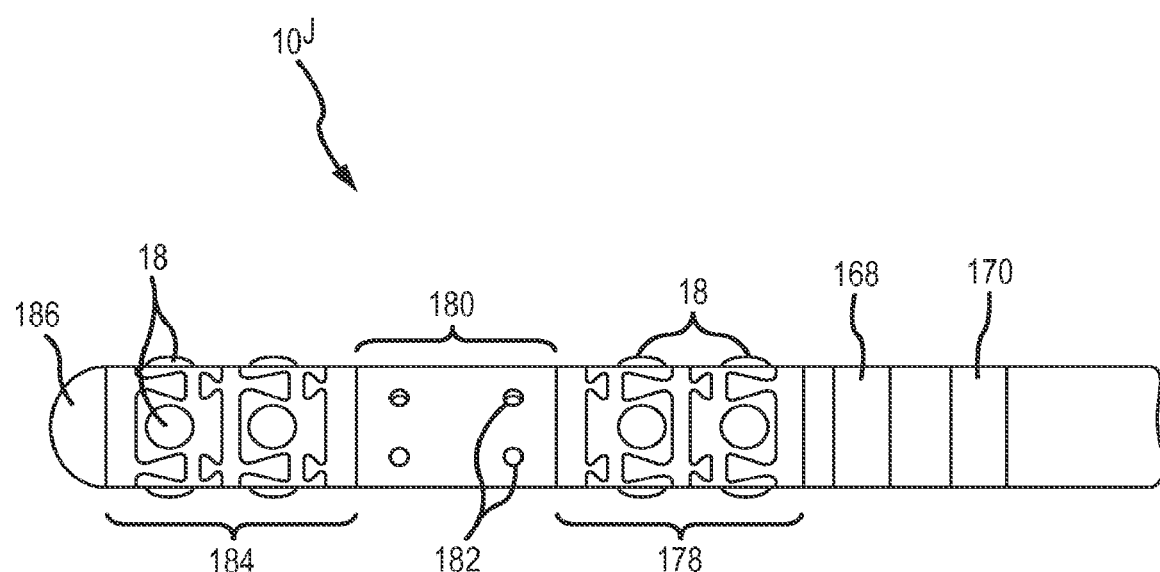
FIG. 32 is another view of the catheter tip depicted in FIG. 31.

FIGS. 31 and 32 depict a tip portion $10^J$ of a map-and-ablate catheter according to a tenth embodiment. Moving distally down the catheter shaft toward the most-distal end, two 1.0 mm ring electrodes are encountered, including a most-proximal ring 170 electrode and a most-distal ring electrode 168. Next, a proximal short flexible array 178 of eight 0.9 mm diameter microelectrodes, mounted in four rows of two microelectrodes, is encountered. In this embodiment, these microelectrodes project from the outer surface of the catheter approximately 0.18 mm and are longitudinally spaced from each other by approximately 1.8 mm. Connected to the distal-side of this short flexible array of microelectrodes is an ablation region 180 that is approximately 3.5 mm long and that includes a plurality of irrigation holes 182. Distal of the ablation region is another, rather short flexible array 184 of microelectrodes. In this particular configuration, the distal flexible array 184 of microelectrodes is similar to the proximal, flexible array 178 of microelectrodes. Finally, in this map ablate catheter, the distal end includes a metallic cap 186 that may be used for mapping, ablation, and/or visualization on fluoroscopy.

FIGS. 33-37 depict a tip portion $10^K$ comprising a flexible array of microelectrodes according to an eleventh embodiment. This planar array (or 'paddle' configuration) of microelectrodes comprises four side-by-side, longitudinally-extending arms 188, 190, 192, 194 forming the flexible framework on which the thirty-two 1.0 mm long×0.8 mm diameter ring electrodes 196 are carried. As discussed further below, a few of these ring electrodes (see, for example, rings 198 and 200 in FIG. 33) may be slightly longer. The four ring-electrode-carrier arms comprise a first outboard arm 188, a second outboard arm 190, a first inboard arm 192, and a second inboard arm 194. These arms are laterally separated from each other by approximately 3.3 mm in this embodiment. Each of the four arms carries eight small ring electrodes 196, spaced along its length. In the depicted embodiment, these small ring-shaped microelectrodes are longitudinally separated from each other by approximately 1.0 mm. Although each of the paddle catheters depicted in FIGS. 33-42 shows four arms, the paddle could comprise more or fewer arms.

Figure 33:
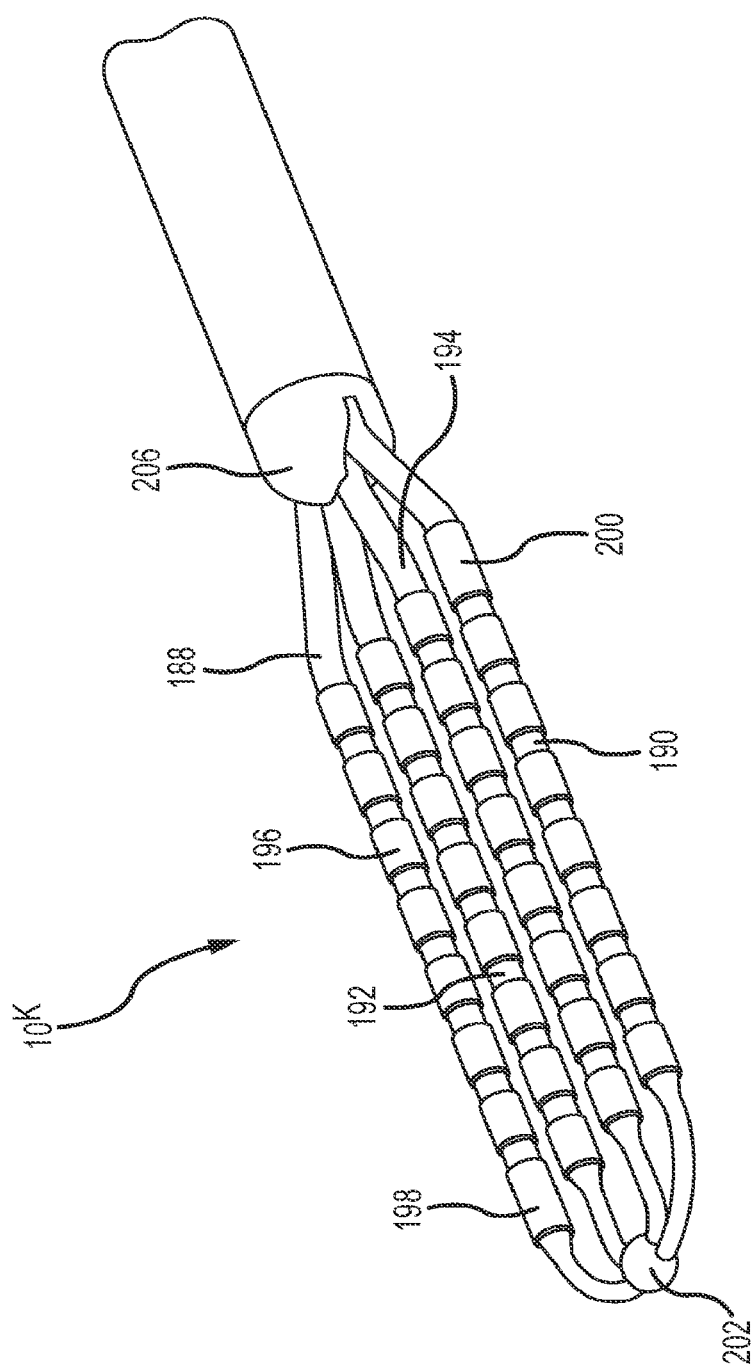
FIG. 33 is a fragmentary, isometric view depicting the tip portion of a high-density mapping catheter according to an eleventh embodiment.
Figure 34:
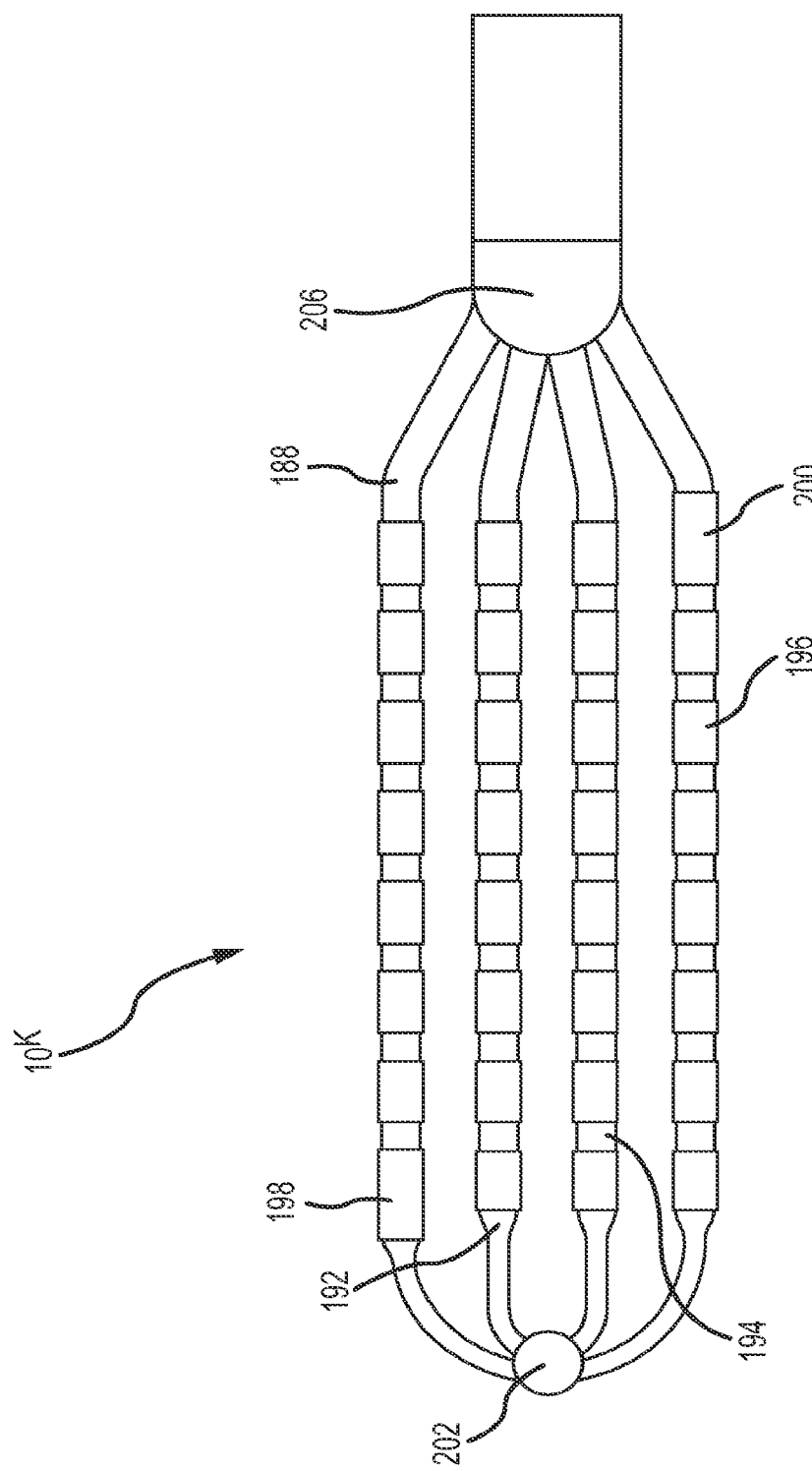
FIG. 34 is a plan view of the catheter tip depicted in FIG. 33.
Figure 35:
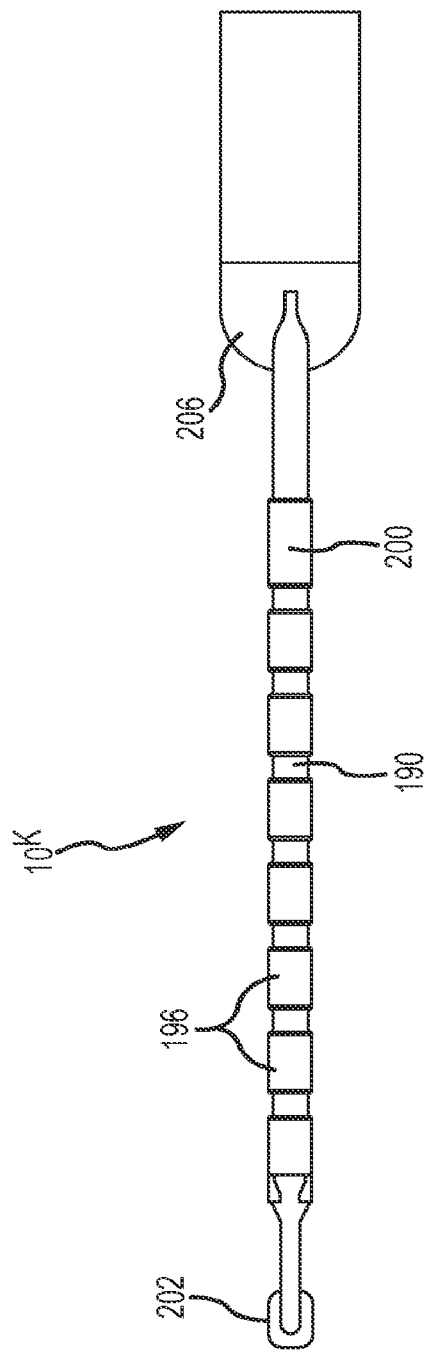
FIG. 35 is an elevational view of the catheter tip depicted in FIGS. 33 and 34.
Figure 36:
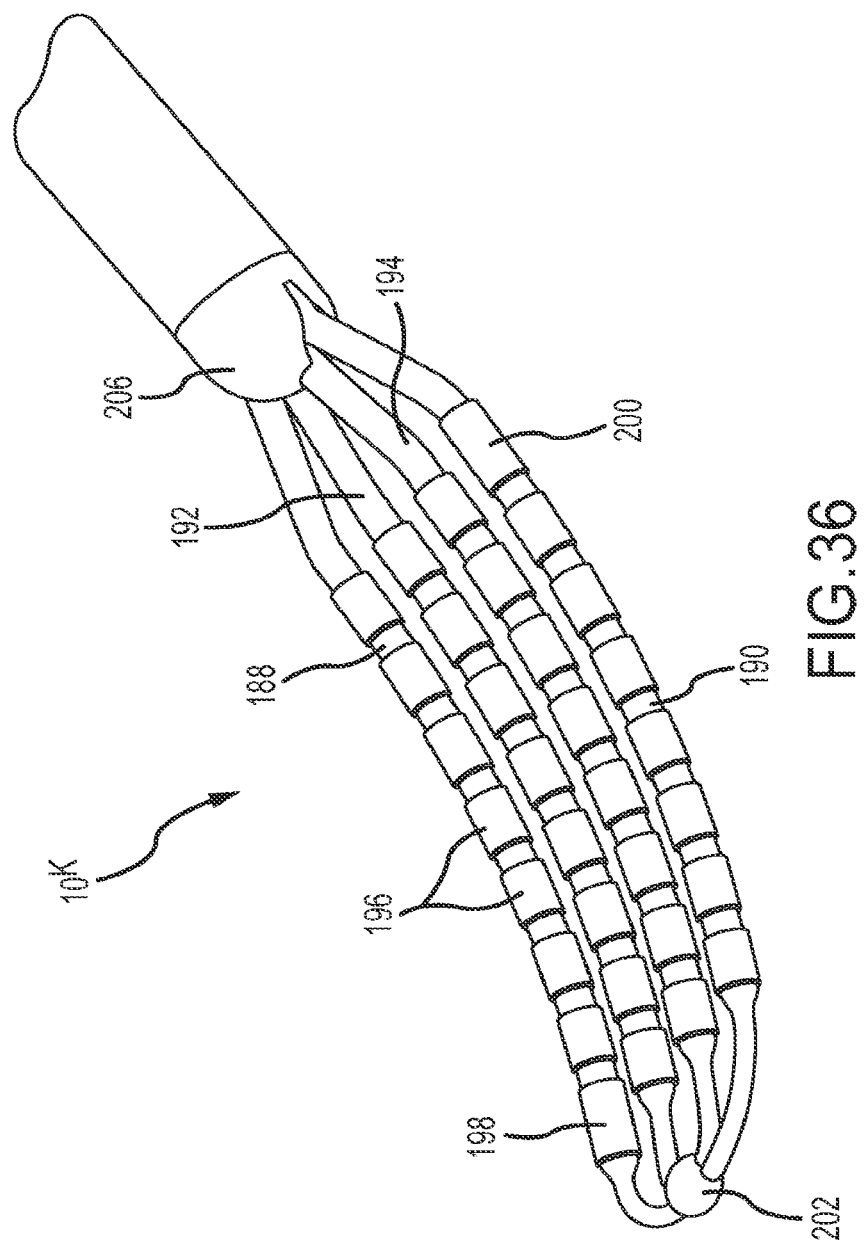
FIG. 36 is a fragmentary, isometric view of the catheter tip depicted in FIGS. 33-35, showing a flexible array of electrodes in a slightly-flexed configuration, simulating contact between the array of electrodes and a cardiac wall.

FIG. 33 is an isometric, fragmentary view of the planar array. As shown to best advantage in FIG. 34, the most-distal ring electrode 198 on the first outboard arm 188 is slightly enlarged as is the most-proximal ring electrode 200 on the second outboard arm 190. These slightly enlarged electrodes 198, 200 (e.g., in the depicted embodiment, these microelectrodes are slightly longer than the other ring electrodes) can be used, for example, for more precise localization of the flexible array in mapping and navigation systems. It is also possible to drive ablation current between these enlarged electrodes, if desired, for bipolar ablation, or, alternatively to drive ablation current in unipolar mode between one or both of these enlarged ring electrodes and, for example a patch electrode located on a patient (e.g., on the patient's back). Similarly, the microelectrodes 196 (on this or any of the other paddle catheters) can be used to perform unipolar or bipolar ablation. Alternatively or concurrently, current could travel between one or more of the enlarged electrodes and any one or all of the microelectrodes. This unipolar or bipolar ablation can create specific lines or patterns of lesions. As also may be seen in FIG. 34, there may be a distal member (or 'button') 202 where one or more of the arms come together. This distal member may be constructed from metal or some other radiopaque material to provide fluoroscopy visualization and semi-independent planar movement between the outer and inner arms.

Figure 37:
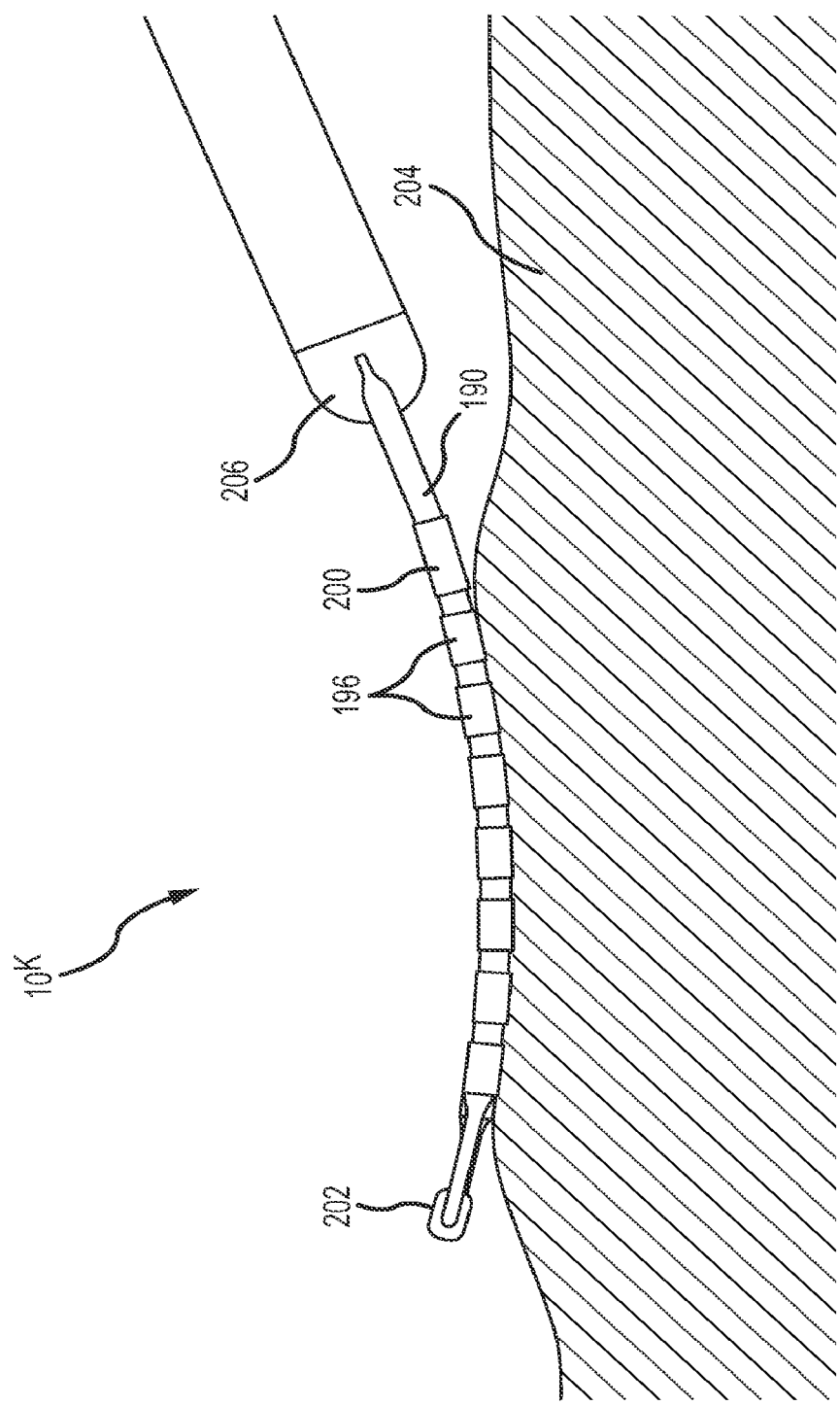
FIG. 37 depicts the catheter shown in FIGS. 33-36 with the array of electrodes riding against trabeculated tissue.

As shown to best advantage in FIG. 37, the planar, flexible arms conform to trabeculated tissue 204, enabling a physician to maintain contact between several of the electrodes and the tissue. This enhances the accuracy, and the corresponding diagnostic value, of the recorded information concerning the heart's electrical activity.

Figure 38:
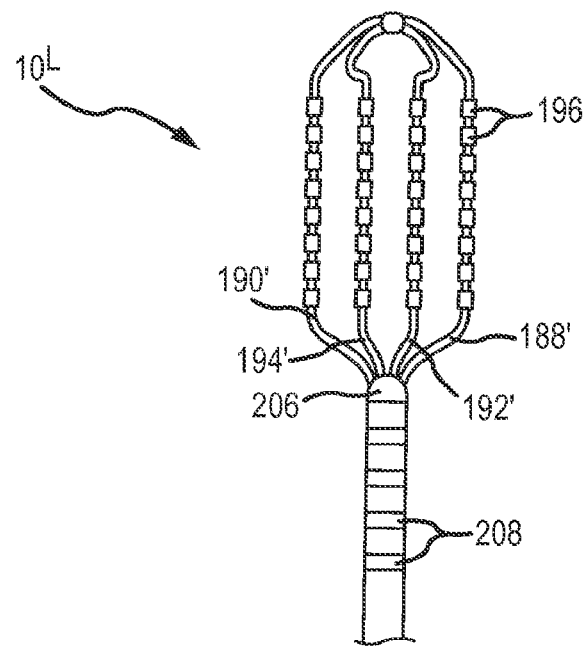
FIG. 38 depicts the distal tip of a high-density mapping catheter according to a twelfth embodiment.
Figure 39:
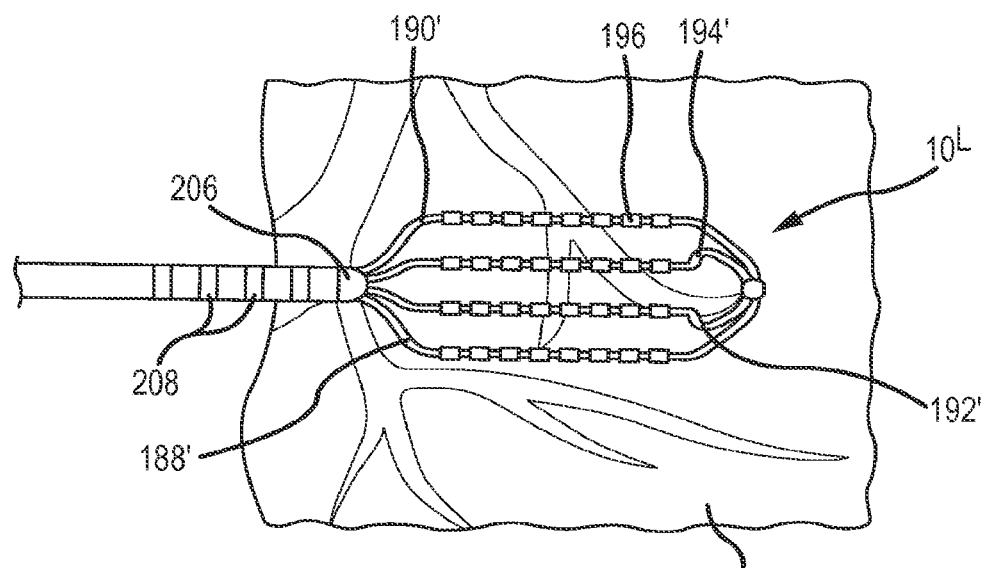
FIG. 39 depicts the distal portion of the high-density mapping catheter also shown in FIG. 38, but overlying vasculature.

FIGS. 38 and 39 depict a flexible array of microelectrodes at the tip portion $10^L$ of a high-density mapping catheter according to a twelfth embodiment. In this configuration, there are four 1.0 mm ring electrodes (depicted with a 2.0 mm longitudinal spacing) mounted on the distal end of the catheter shaft, proximal to a proximal bushing 206 and to the proximal ends of ring electrode carrier arms 188', 190', 192', 194'. In this embodiment, each of the four electrode carrying arms has eight small ring electrodes 196 (microelectrodes) mounted on it. The four arms are designed to maintain the thirty-two small ring electrodes in a spaced relationship so that each small ring electrode can capture separate data about the electrical activity of the cardiac tissue adjacent to the microelectrodes.

Figure 40:
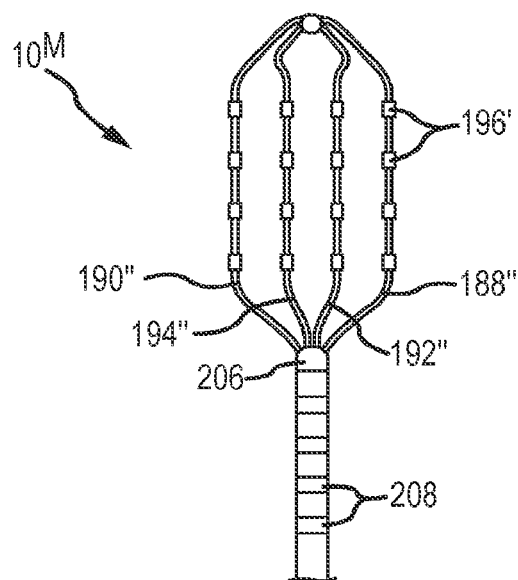
FIG. 40 depicts a tip portion of a high-density mapping catheter according to a thirteenth embodiment.
Figure 41:
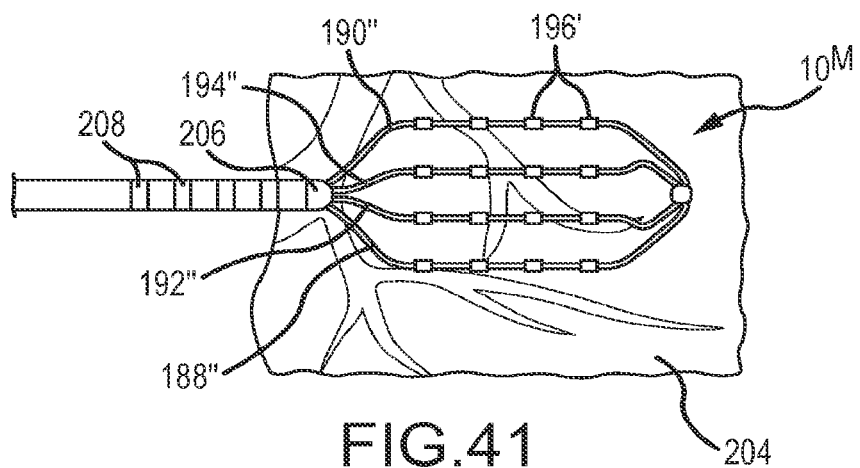
FIG. 41 depicts the distal portion of the high-density mapping catheter also shown in FIG. 40, but overlying vasculature.
Figure 42:
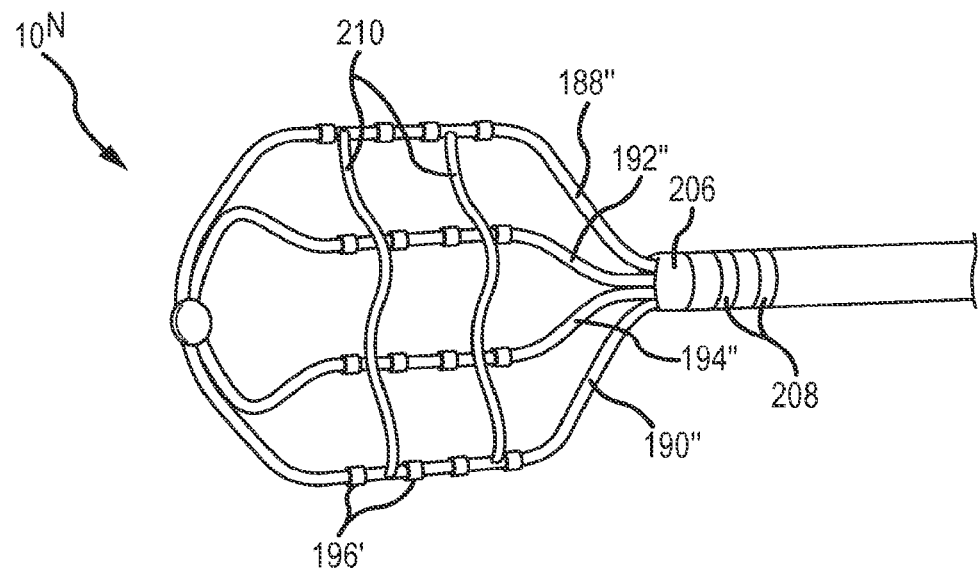
FIG. 42 is an isometric view of a high-density mapping catheter similar to that shown in FIGS. 40 and 41, but also comprising two tethers.

FIGS. 40-42 depict two variations $10^M$, $10^N$ of a similar tip portion comprising a flexible array of microelectrodes 196'. In both variations of this particular configuration, there are sixteen small ring electrodes 196' mounted on four small arms 188", 190", 192", 194" rather than the thirty-two ring electrodes 196 depicted in FIGS. 38 and 39. These small ring electrodes (1.0 mm long×0.8 mm diameter) are longitudinally separated from each other by approximately 3.0 mm in this embodiment, and the electrode carrying arms are laterally separated from each other by approximately 4.0 mm. Further, in the variation $10^N$ depicted in FIG. 42, the high-density mapping catheter also includes two tethers 210 extending transverse across and interconnecting the four electrode carrying arms. Although two tethers are shown in FIG. 42, any number of tethers could be used, including a single tether. The tether or tethers 210 help maintain a predictable relationship between the electrode carrying arms 188", 190", 192", 194" by controlling, for example, how each electrode carrying arm may move relative to the other electrode carrying arms. Each tether 210 may comprise a tensile element, such as slender mono- or multi-filament nylon thread or suture-like material. The tethers may be connected with or to the electrode carrying arm in a variety of ways. In FIG. 42, for example, the tethers 210 have been adhered or ultrasonically welded to each of the electrode carrying arms 188", 190", 192", 194". Alternatively, a tether could be tied to or looped around the arms. Reflowing the device during the manufacturing process may allow the tether or tethers to become incorporated into the arms polymer insulation, thereby securing the tether to the arms and minimizing the need for tying, looping, gluing, or otherwise attaching the tethers to the arms. The tethers 210 are configured to also collapse or fold during insertion of the catheter into a delivery sheath or introducer.

Figure 43:
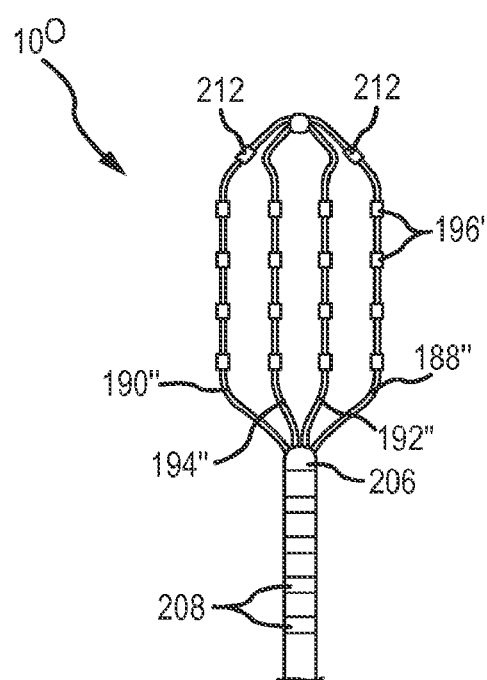
FIG. 43 depicts the distal tip of a high-density mapping catheter according to a fourteenth embodiment.

FIG. 43 depicts yet another embodiment of a tip portion 10$^O$ comprising a flexible array of microelectrodes. This configuration is most similar to the first variation 10$^M$ of the thirteenth embodiment, which is depicted in FIGS. 40 and 41. However, in the fourteenth embodiment, there are two additional ring electrodes 212 mounted near the distal end of each outboard arm.

Figure 44:
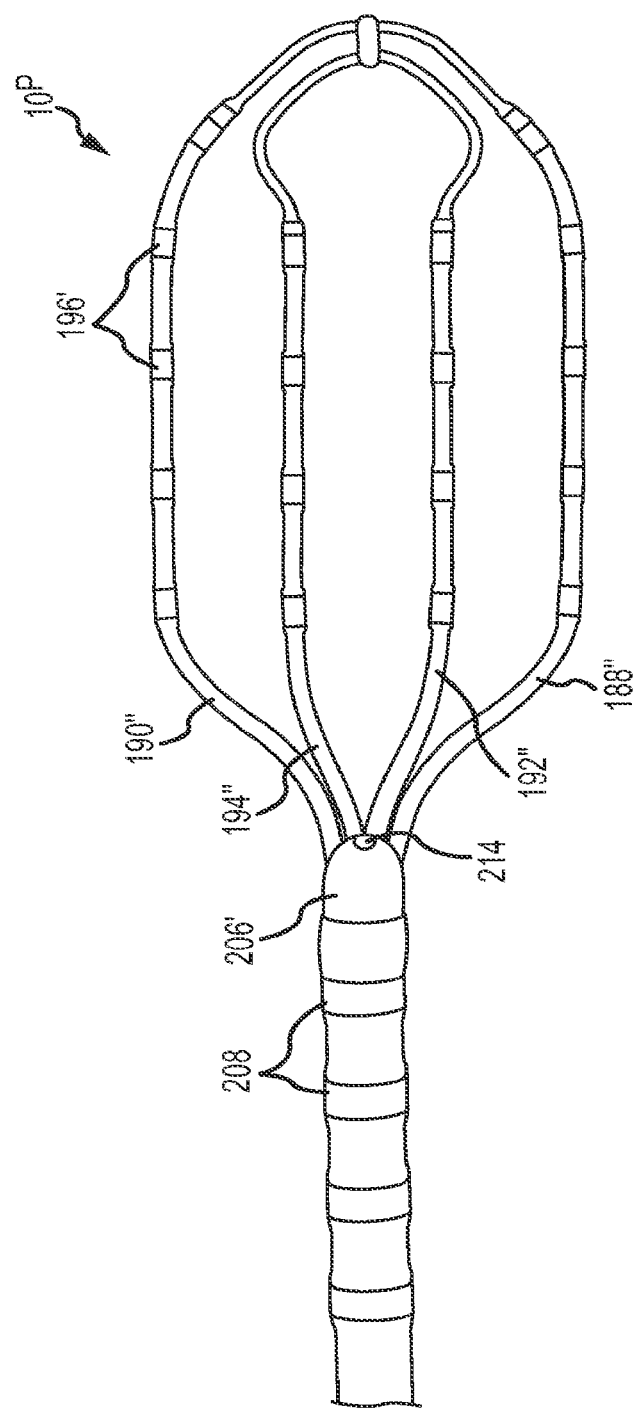
FIG. 44 depicts a high-density mapping catheter most similar to the catheter depicted in FIG. 43, but also comprising an irrigation port near a distal edge of a proximal bushing.
Figure 45:
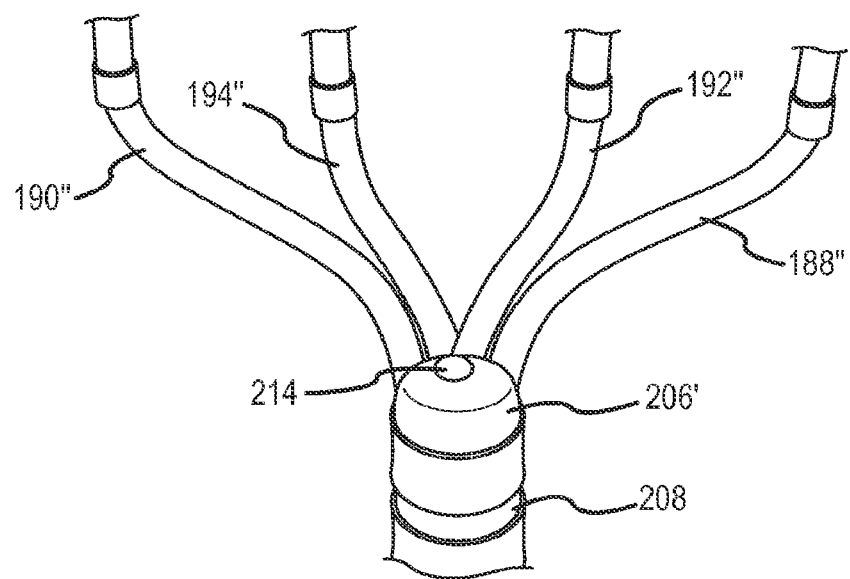
FIG. 45 is an enlarged, fragmentary view of a portion of the high-density mapping catheter depicted in FIG. 44, clearly showing the irrigation port.

FIG. 44 depicts an alternative variation of the high-density mapping catheter embodiment 108 depicted in FIG. 43. In particular, in FIG. 44, an irrigation port 214 is present at the distal end of a proximal bushing 206', and the irrigation port is positioned to deliver irrigant to or near the point where the electrode carrying arms exit from the distal end of the proximal bushing that is mounted on the distal end of the catheter shaft in this embodiment. If desired, a second irrigation port (not shown) may be located near the distal intersection of the electrode carrying arms. In fact, if desired, multiple irrigation ports (not shown) could be present at various positions along the electrode carrying arms 188", 190", 192", 194". FIG. 45 is an enlarged, fragmentary view of the irrigation port 214 on the proximal bushing 206'. Further, while only one irrigation port 214 is illustrated on the proximal bushing 206', multiple irrigation ports could be present on the proximal bushing (e.g., one or more on each side of the planar array of microelectrodes) to provide more uniform irrigant distribution at or near the proximal apex of the arms 188", 190", 192", 194". Likewise, a distal irrigation port set (not shown) comprising multiple ports could be included at or near the distal apex of the arms 188", 190", 192", 194".

Figure 46:
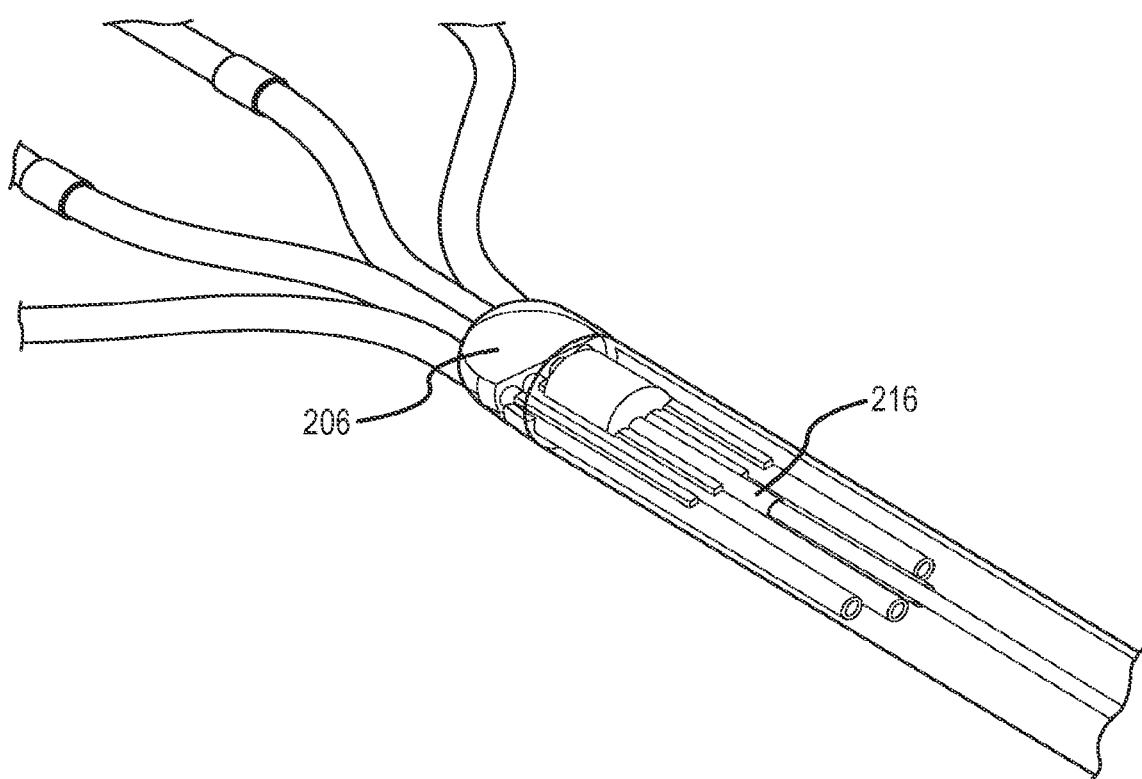
FIG. 46 is an enlarged, isometric view of an embodiment of a high-density mapping catheter comprising a location sensor mounted in the catheter shaft proximal to a proximal bushing.

FIG. 46 is a fragmentary, isometric view of the distal portion of the catheter shaft of a high-density mapping catheter. In this view, portions of the catheter shaft have been removed to reveal a sensor 216 located just proximal to the proximal bushing. A variety of sensors may be incorporated at this location, or at similar locations, in the high-density mapping catheters described herein. These sensors may be mounted in the catheter shaft, as shown in FIG. 46, or they may be mounted at other locations (e.g., along the electrode carrying arms of the high-density mapping paddle and/or at the distal apex or joint of the tip portion). In one embodiment, the sensor 216 is a magnetic field sensor configured for use with an electromagnetic localization system such as the MediGuide™ System sold by St. Jude Medical, Inc. of St. Paul, Minn.

Figure 47:
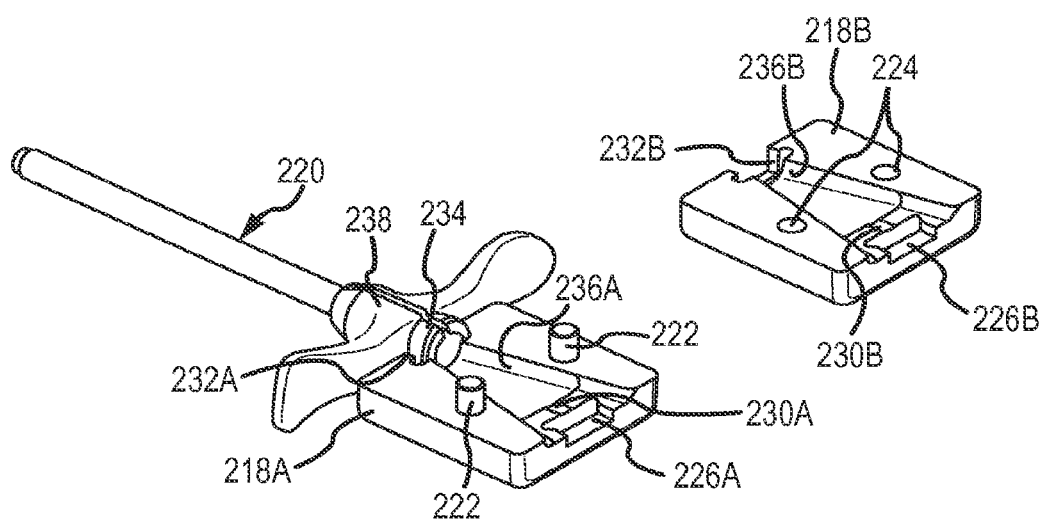
FIG. 47 is an exploded, isometric view of a delivery adapter and a guiding sheath.

FIG. 47 is an exploded, isometric view of one embodiment of a delivery adapter 218 designed to facilitate delivery of a paddle catheter into and through a guiding sheath or introducer 220 having a circular cross section. As depicted in this figure, the delivery adapter 218 comprises a first portion 218A having pins 222 extending therefrom, and a second portion 218B having complementary pin-receiving holes 224 therein. When these portions 218A, 218B are assembled, a proximal pocket configured to support or hold the distal end of a dilator hub 228 (labeled in FIGS. 48A and 48B) is formed. In particular, the first portion 218A of the delivery adapter includes a first part 226A of that pocket, and the second portion 218B of the delivery adapter comprises a second part 226B of the pocket. In this particular embodiment, a dilator shaft channel is also present and comprises a first trough 230A formed in the first portion 218A of the delivery adapter 218 and a second trough 230B formed in the second portion 218B of the delivery adapter 218. Also, the distal side of the delivery adapter, in this embodiment, comprises a threaded hole (e.g., a female luer lock) 232A, 232B adapted to thread onto a shaft or fitting (e.g., a male luer lock) 234 extending proximally from the proximal end of the guiding sheath 220.

As best seen in FIG. 47, the interior of the delivery adapter, between the proximal pocket 226A, 226B and the threaded hole 232A, 232B defines a hollow compression or folding cone 236A, 236B. In one embodiment, for example, the lateral cross-sectional shape of the proximal end of this compression cone is elliptical or nearly elliptical, and the lateral cross-sectional shape of the distal-most portion of the compression cone is circular or near circular, matching the channel through a hub 238 of the guiding sheath 220. The compression cone is thereby configured or adapted to compress the relatively flat paddle of the high-density mapping catheter into a configuration having a substantially circular cross-sectional shape or other shape that fits into the proximal opening in the guiding sheath hub 238. It should also be noted that the delivery adapter may be splittable for easy removal when used with a splittable guiding sheath.

Figure 48A:
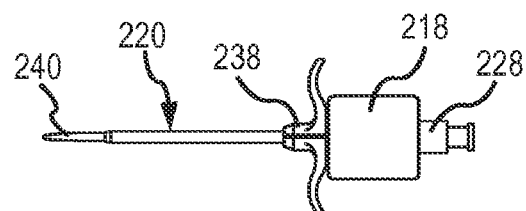
FIGS. 48A-48F depict a series of views showing how a delivery adapter such as the one depicted in FIG. 47 may be used with a dilator for delivering a paddle catheter into a guiding sheath.
Figure 48B:

Referring now most specifically to the various views comprising FIGS. 48A-48F, one use of the delivery adapter 218 just described in connection with FIG. 47 is described next. In this use, a dilator 240 is inserted into and through the delivery adapter 218 and seated in the pocket 226A, 226B formed in the proximal side of the assembled delivery adapter. The assembled delivery adapter 218, with the dilator 240 in place, is then mounted to the guiding sheath 220 as shown in FIG. 48A. The dilator 240, shown by itself in FIG. 48B, is then removed from the delivery adapter 218 and guiding sheath 220, as may be seen in the left-hand portion of FIG. 48C.

Figure 48C:
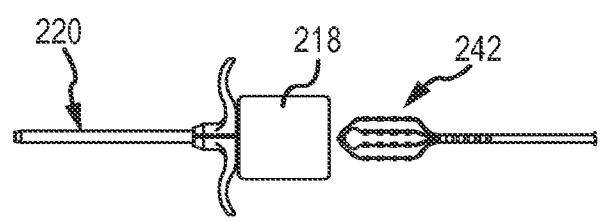
Figure 48D:
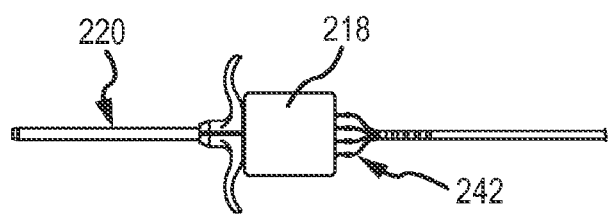
Figure 48E:
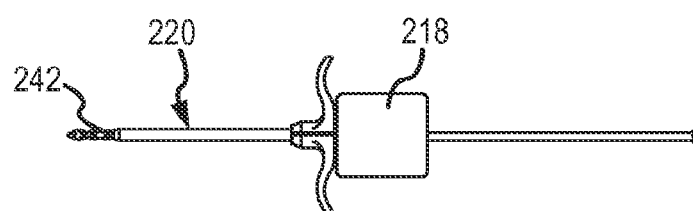
Figure 48F:
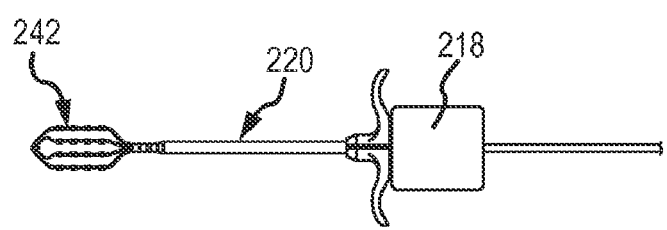

Next, as also shown in view FIG. 48C, the paddle 242 of a high-density mapping catheter is inserted into the proximal end of the compression cone 236A, 236B of the delivery adapter. In FIG. 48D, the electrode carrying arms of the paddle have been inserted further into the compression cone. As the electrode carrying arms of the paddle impact the angled side surfaces of the compression cone formed in the delivery adapter 218, the electrode carrying arms are compressed towards each other. When the arms have been sufficiently compressed together (i.e., into a side-by-side, touching or near-touching configuration), the paddle then fits into the proximal end of the port through the guiding sheath or introducer 220 and may be pushed through the hemostasis valve (not shown) in the hub 238 at the proximal end of the guiding sheath 220. As shown in FIG. 48E, as the paddle portion 242 of the high-density mapping catheter exits from the distal end of the guiding sheath 220, the electrode carrying arms comprising the paddle remain compressed together. Once the electrode carrying arms of the paddle exit from the distal end of the shaft or tube of the guiding sheath, the electrode carrying arms expand back into the paddle configuration, as best shown in FIG. 48F.

In each of the embodiments depicted in, for example, FIGS. 33-46, one or more of the ring electrodes 208 could be used to send pacing signals to, for example, cardiac tissue. Further, the arms (or the understructure of the arms) comprising the paddle structure (or multi-arm, electrode-carrying, flexible framework) at the distal end of the catheters depicted in FIGS. 33-46 are preferably constructed from a flexible or spring-like material such as Nitinol. The construction (including, for example, the length and/or diameter of the arms) and material of the arms can be adjusted or tailored to be created, for example, desired resiliency, flexibility, foldability, conformability, and stiffness characteristics, including one or more characteristics that may vary from the proximal end of a single arm to the distal end of that arm, or between or among the plurality of arms comprising a single paddle structure. The foldability of materials such as Nitinol provide the additional advantage of facilitating insertion of the paddle structure into a delivery catheter or introducer, whether during delivery of the catheter into the body or removal of the catheter from the body at the end of a procedure. Although a short guide sheath 220 (used, for example, for epicardial access) is depicted in FIGS. 47 and 48A-48F, a longer guide sheath (used, for example, to access the heart from a femoral access point) could be used to introduce the flexible high-density mapping and ablation tips described herein.

Among other things, the disclosed catheters, with their plurality of microelectrodes, are useful to (1) define regional propagation maps on one centimeter square areas within the atrial walls of the heart; (2) identify complex fractionated atrial electrograms for ablation; (3) identify localized, focal potentials between the microelectrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact. Additionally, the catheters described herein may be useful for epicardial and/or endocardial use. For example, the planar array embodiments depicted in FIGS. 33-48F may be used in an epicardial procedure where the planar array of microelectrodes is positioned between the myocardial surface and the pericardium. Alternatively the planar array embodiments may be used in an endocardial procedure to quickly sweep and/or analyze the inner surfaces of the myocardium and quickly create high-density maps of the heart tissue's electrical properties.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A high-density mapping catheter comprising:
a catheter shaft comprising a proximal end and a distal end, the catheter shaft defining a catheter shaft longitudinal axis extending between the proximal end and the distal end;
a flexible tip portion fixed adjacent to the distal end of the catheter shaft, the flexible tip portion comprising a flexible framework comprising nonconductive material forming a plurality of electrode-carrying arms fixed adjacent to the distal end of the catheter shaft to prevent longitudinal movement between the electrode-carrying arms and the distal end of the catheter shaft, wherein each of the plurality of electrode-carrying arms converges with at least one other of the plurality of electrode-carrying arms at a distal end of the flexible tip portion; and
a plurality of microelectrodes mounted on the flexible framework and forming a flexible, planar array of microelectrodes adapted to conform to tissue, wherein the plurality of microelectrodes are mapping electrodes, wherein the flexible framework is configured to facilitate relative movement among at least some of the plurality of microelectrodes relative to other of the plurality of microelectrodes, and wherein the nonconductive material insulates each of the plurality of microelectrodes from other of the plurality of microelectrodes.

2. The high-density mapping catheter of claim 1, wherein the plurality of microelectrodes are arranged in a plurality of rows, wherein each row is distributed along a different one of the plurality of electrode-carrying arms and the plurality of rows is aligned parallel to the catheter shaft longitudinal axis.

3. The high-density mapping catheter of claim 2, wherein the plurality of electrode-carrying arms are configured to maintain the plurality of microelectrodes in the plurality of rows in a spaced relationship such that each of the plurality of microelectrodes can capture separate data about the electrical activity of cardiac tissue adjacent to the plurality of microelectrodes.

4. The high-density mapping catheter of claim 1, wherein the plurality of microelectrodes comprise between four and sixty-four individual microelectrodes.

5. The high-density mapping catheter of claim 1, further comprising at least one ring electrode mounted on the catheter shaft adjacent to the flexible, planar array of microelectrodes.

6. The high-density mapping catheter of claim 1, further comprising at least one location sensor.

7. The high-density mapping catheter of claim 6, wherein the at least one location sensor is mounted in or on at least one of the following: the catheter shaft and the distal end of the flexible tip portion.

8. The high-density mapping catheter of claim 6, wherein the at least one location sensor is a magnetic field sensor.

9. The high-density mapping catheter of claim 1, wherein the flexible, planar array of microelectrodes comprises a two-sided planar array of microelectrodes, wherein the microelectrodes are configured for contacting tissue on a front side and a back side of the planar array.

10. The high-density mapping catheter of claim 1, wherein the microelectrodes are ring electrodes.

11. A catheter comprising:
an elongated catheter body comprising a proximal end and a distal end, and defining a catheter longitudinal axis extending between the proximal and distal ends; and
a flexible tip assembly fixed at the distal end of the catheter body and comprising a flexible framework of nonconductive material, wherein the flexible framework comprises a plurality of electrode-carrying arms adapted to conform to tissue, wherein each of the plurality of electrode-carrying arms converges with at least one other of the plurality of electrode-carrying arms at a distal end of the flexible tip assembly, wherein each of the plurality of electrode-carrying arms is fixed adjacent to the distal end of the elongated catheter body to prevent longitudinal movement between the electrode-carrying arms and the distal end of the elongated catheter body, and wherein the flexible tip assembly further comprises:
a plurality of microelectrodes arranged in a flexible, planar array comprising a plurality of rows of longitudinally-aligned microelectrodes aligned parallel to the catheter longitudinal axis and mounted on the plurality of electrode-carrying arms so that at least some of the plurality of microelectrodes are moveable relative to other of the plurality of microelectrodes, wherein each row of microelectrodes is distributed along a different one of the plurality of electrode-carrying arms.

12. The catheter of claim 11, wherein the plurality of electrode-carrying arms are configured to maintain the plurality of microelectrodes in the plurality of rows in a spaced relationship such that each of the plurality of microelectrodes can capture separate data about the electrical activity of cardiac tissue adjacent to the plurality of microelectrodes.

13. The catheter of claim 11, wherein the plurality of microelectrodes are equally spaced along each of the plurality of electrode-carrying arms.

14. The catheter of claim 11, wherein the plurality of microelectrodes are configured for use as mapping electrodes.

15. The catheter of claim 14, wherein the plurality of microelectrodes are configured for use in unipolar or bipolar ablation.

16. The catheter of claim 15, further comprising a temperature sensor.

17. The catheter of claim 15, further comprising an irrigation port configured to deliver an irrigant on or adjacent to the planar array of microelectrodes.

18. The catheter of claim 15, further comprising an internal fluid delivery lumen configured to be fluidly coupled to a source of irrigant and configured to deliver the irrigant to the flexible tip assembly.

19. The catheter of claim 11, wherein the flexible, planar array of microelectrodes comprises a two-sided planar array of microelectrodes, wherein the microelectrodes are configured for contacting tissue on a front side and a back side of the planar array.

20. The catheter of claim 11, wherein the microelectrodes are ring electrodes.

* * * * *